(12) United States Patent
Rudolph et al.

(10) Patent No.: US 8,907,110 B2
(45) Date of Patent: Dec. 9, 2014

(54) BENZODIOXEPIN-3-ONE COMPOUNDS AS DYES OR AS FLUORESCENT EMITTERS

(71) Applicant: Merck Patent GmbH, Darmstadt (DE)

(72) Inventors: Thomas Rudolph, Darmstadt (DE); Philipp Buehle, Zwingenberg (DE); Ralf Rosskopf, Muenster (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/351,645

(22) PCT Filed: Sep. 17, 2012

(86) PCT No.: PCT/EP2012/003869
§ 371 (c)(1),
(2), (4) Date: Apr. 14, 2014

(87) PCT Pub. No.: WO2013/053422
PCT Pub. Date: Apr. 18, 2013

(65) Prior Publication Data
US 2014/0234238 A1 Aug. 21, 2014

(30) Foreign Application Priority Data
Oct. 14, 2011 (DE) .......................... 10 2011 116 165

(51) Int. Cl.
| | | |
|---|---|---|
| C07D 321/10 | (2006.01) | |
| C07D 323/02 | (2006.01) | |
| C09B 13/00 | (2006.01) | |
| C07D 405/14 | (2006.01) | |
| C07D 231/10 | (2006.01) | |
| C07D 407/14 | (2006.01) | |
| C07D 409/14 | (2006.01) | |
| C09K 11/06 | (2006.01) | |
| A61K 8/49 | (2006.01) | |
| A61Q 5/02 | (2006.01) | |
| A61Q 5/06 | (2006.01) | |
| A61Q 17/04 | (2006.01) | |
| A61Q 19/04 | (2006.01) | |
| C09B 57/00 | (2006.01) | |
| H01L 51/00 | (2006.01) | |
| A61Q 5/10 | (2006.01) | |
| A61Q 5/12 | (2006.01) | |
| A61Q 19/10 | (2006.01) | |
| H01L 51/50 | (2006.01) | |

(52) U.S. Cl.
CPC .............. *C09B 13/00* (2013.01); *C07D 405/14* (2013.01); *C07D 231/10* (2013.01); *C07D 407/14* (2013.01); *C07D 409/14* (2013.01); *C09K 11/06* (2013.01); *A61K 8/4973* (2013.01); *A61Q 5/02* (2013.01); *A61Q 5/065* (2013.01); *A61Q 17/04* (2013.01); *A61Q 19/04* (2013.01); *C09B 57/00* (2013.01); *H01L 51/0059* (2013.01); *H01L 51/0068* (2013.01); *H01L 51/0072* (2013.01); *A61K 8/4986* (2013.01); *A61Q 5/10* (2013.01); *H01L 51/0073* (2013.01); *H01L 51/0074* (2013.01); *A61Q 5/12* (2013.01); *A61Q 19/10* (2013.01); *A61K 2800/434* (2013.01); *H01L 51/5012* (2013.01); *H01L 51/5032* (2013.01); *Y02E 10/549* (2013.01); *C09K 2211/1007* (2013.01); *C09K 2211/1011* (2013.01); *C09K 2211/1014* (2013.01); *C09K 2211/1088* (2013.01)
USPC .......................................................... 549/350

(58) Field of Classification Search
None
See application file for complete search history.

(56) References Cited

U.S. PATENT DOCUMENTS

2013/0309184 A1 11/2013 Rudolph et al.

FOREIGN PATENT DOCUMENTS

| EP | 2108646 A1 | 10/2009 |
|---|---|---|
| WO | 2012107158 A1 | 8/2012 |

OTHER PUBLICATIONS

International Search Report for PCT/EP2012/003869 dated Jan. 17, 2013.
Abaee, M. S. et al., "The first synthesis of Bis(arylmethylidene)dioxin-5-ones: Potential Scaffolds to access vicinal tricarbonyl derivatives," Synthesis, May 2008, vol. 13, No. 21, pp. 2122-2126.
English Abstract of EP2108646, Publication Date: Oct. 14, 2009.

*Primary Examiner* — Sun Jae Yoo
(74) *Attorney, Agent, or Firm* — Millen, White, Zelano & Branigan, P.C.

(57) ABSTRACT

The invention relates to specific benzodioxepin-3-one compounds, to a process for the preparation thereof and to the use thereof as dyes or as fluorescent emitters for organic electroluminescent devices (OLEDs) or for organic light-emitting electrochemical cells (OLECs), and to corresponding electronic devices.

20 Claims, No Drawings

BENZODIOXEPIN-3-ONE COMPOUNDS AS DYES OR AS FLUORESCENT EMITTERS

The invention relates to specific benzodioxepin-3-one compounds, to a process for the preparation thereof and to the use thereof as dyes or as fluorescent emitters for organic electroluminescent devices (OLEDs) or for organic light-emitting electrochemical cells (OLECs), and to corresponding electronic devices.

A multiplicity of dyes is currently known for the dyeing of matrices, such as, for example, skin, hair, nails or textiles. Direct dyes, for example, are able to associate onto the matrix and/or form covalent chemical bonds with the matrix. In other dyeing processes, a soluble precursor of the dye can be converted into the dye on the matrix during the dyeing process. Furthermore, in the case of, for example, dispersion dyeing, sparingly soluble or insoluble dyes are able to diffuse into the matrix during treatment of the matrix with a dispersion of this type and possibly form a covalent bond with the matrix. The dyeing of the matrix can thus take place in different ways and give a different result with respect to the binding character and also the colour result.

Various dyes have been approved for the dyeing of foods or cosmetic compositions, last amended by the regulation of 9 Aug. 2010 (BGBl. I p. 1146). The number of lipophilic dyes approved for use is very limited. The two dyes C.I. 75300 (E100, curcumin) and C.I. 40800 (E160a, beta-carotene) may be mentioned by way of example. Both dyes have the deficiency of unsatisfactory stabilities and can be decomposed, for example, by UV or visible light, a change in the pH, heat or by oxidation.

On use of, in particular synthetic, dyes, there may additionally be low tolerance, in particular in the human area of application.

Accordingly, there continues to be a demand for dyes which are, inter alia, tolerated and in particular skin-tolerated, have high substantivity to the substrate to be dyed and whose colours are distinguished by high light, heat, pH and oxidation stability.

There likewise continues to be a demand for compounds which can be used for the protection of skin and hair against photoageing by light, in particular against photoageing caused by visible light.

Accordingly, the present invention is concerned with the problem of providing alternative dyes having improved properties for the dyeing of a very wide variety of substrates or preparing alternative compounds which are capable of protecting skin and hair by photoageing by visible light.

This problem is solved in accordance with the invention by the subject-matters of the independent claims. Advantageous embodiments are the subject-matter of the dependent claims.

Surprisingly, it has been found that the [1,5]-benzodioxepin-3-one compounds of the formula I, as described below, are dyes having the desired property profile. It has furthermore been found that the compounds of the formula I, as described below, are likewise fluorescent emitters which are suitable for use in electronic devices, in particular for organic electroluminescent devices (OLEDs) or organic light-emitting electrochemical cells (OLECs). It has furthermore been found that the compounds of the formula I, as described below, can be employed for the protection of skin and hair against photoageing by light, in particular for protection against photoageing induced by visible light.

The invention therefore relates to the compounds of the formula I,

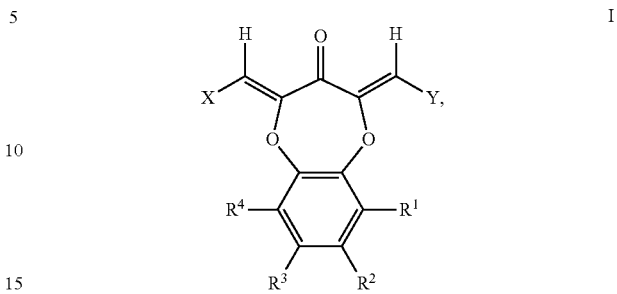

where $R^1$, $R^2$, $R^3$ and $R^4$ each, independently of one another, denote H, $NO_2$, Hal, a straight-chain or branched alkyl group having 1 to 20 C atoms or a straight-chain or branched alkoxy group having 1 to 20 C atoms, X and Y each, independently of one another, denote
an aryl or heteroaryl group having 5 to 24 ring atoms which is unsubstituted or mono- or polysubstituted by R, or
a group of aryl and/or heteroaryl groups having 5 to 24 ring atoms which are unsubstituted or mono- or polysubstituted by R, where the aryl and/or heteroaryl groups in this group are each linked, independently of one another, singly or multiply, by a single bond, a double bond, conjugated double bonds, a C atom or by a unit of the formula $(CHR^5)_n$-$(Het)_o$-$(CHR^5)_p$, R in each case, independently of one another on each occurrence, denotes D, Hal, alkyl, OH, O-alkyl, O-aryl, S-alkyl, $NH_2$, NHalkyl, $N(alkyl)_2$, $N(aryl)_2$, cycloalkyl, O-cycloalkyl, S-cycloalkyl, NH-cycloalkyl, $N(cycloalkyl)_2$, CN, $NO_2$, $Si(alkyl)_3$, $B(OR^6)_2$, $C(O)R^6$, $P(O)(R^6)_2$, $S(O)R^6$, $S(O)_2R^6$, a straight-chain or branched alkenyl group having 2 to 20 C atoms and one or more double bonds or a straight-chain or branched alkynyl group having 2 to 20 C atoms and at least one triple bond and optionally one or more double bonds, $R^5$ in each case, independently of one another on each occurrence, denotes H, D, Hal, alkyl, OH, O-alkyl, O-aryl, S-alkyl, $NH_2$, NHalkyl, $N(alkyl)_2$, $N(aryl)_2$, cycloalkyl, O-cycloalkyl, S-cycloalkyl, NH-cycloalkyl, $N(cycloalkyl)_2$, CN, $NO_2$, $Si(alkyl)_3$, $B(OR^6)_2$, $C(O)R^6$, $C(O)_2R^6$, $P(O)(R^6)_2$, $S(O)R^6$, $S(O)_2R^6$, a straight-chain or branched alkenyl group having 2 to 20 C atoms and one or more double bonds or a straight-chain or branched alkynyl group having 2 to 20 C atoms and at least one triple bond and optionally one or more double bonds, $R^6$ in each case, independently of one another, denotes H, D, OH, alkyl, aryl, cycloalkyl, Oalkyl, Oaryl or O-cycloalkyl, alkyl denotes a straight-chain or branched alkyl group having 1 to 20 C atoms, which may be partially or fully substituted by halogen, cycloalkyl denotes a cyclic saturated or partially unsaturated cycloalkyl group having 3 to 7 C atoms, aryl denotes an aryl group having 6 to 10 C atoms, which may be mono- or polysubstituted by alkyl, Oalkyl, $N(alkyl)_2$ or Hal, Hal denotes F, Cl, Br or I, Het denotes O, S, —N═N—, NH or NR, n denotes an integer from 0 to 5, o denotes 0 or 1, p denotes an integer from 0 to 5, n+o+p denotes at least the number 1 and salts, tautomers, steroisomers thereof, including mixtures thereof in all ratios and/or solvates.

For the purposes of the invention, the compounds of the formula I are defined in such a way that they are also taken to mean pharmaceutically or cosmetically usable derivatives, salts, hydrates, solvates and isomers (such as, for example, stereoisomers, diastereomers, enantiomers, racemates, tautomers, E-Z isomers). Solvates of the compounds are taken to mean adductions of inert solvent molecules onto the compounds which form owing to their mutual attractive force. Solvates are, for example, mono- or dihydrates or alcoholates. Pharmaceutically or cosmetically usable derivatives are taken to mean, for example, the salts of the compounds according to the invention.

A straight-chain or branched alkyl group having 1 to 8 C atoms is, for example, methyl, ethyl, isopropyl, propyl, butyl, sec-butyl or tert-butyl, furthermore pentyl, 1-, 2- or 3-methylbutyl, 1,1-, 1,2- or 2,2-dimethylpropyl, 1-ethylpropyl, n-hexyl, n-heptyl or n-octyl.

A straight-chain or branched alkyl group having 1 to 20 C atoms encompasses the group of straight-chain or branched alkyl group having 1 to 8 C atoms described above and nonanyl, decanyl, undecanyl, dodecanyl, tridecanyl, tetradecanyl, pentadecanyl, hexadecanyl, heptadecanyl, octadecanyl, nonadecanyl and eicosanyl.

A straight-chain or branched alkyoxy group having 1 to 20 C atoms is, for example, methoxy, ethoxy, isopropyloxy, propyloxy, butyloxy, sec-butyloxy, tert-butyloxy, pentyloxy, 1-, 2- or 3-methylbutyloxy, 1,1-, 1,2- or 2,2-dimethylpropyloxy, 1-ethylpropyloxy, n-hexyloxy, n-heptyloxy, n-octyloxy, nonanyloxy, decanyloxy, undecanyloxy, dodecanyloxy, tridecanyloxy, tetradecanyloxy, pentadecanyloxy, hexadecanyloxy, heptadecanyloxy, octadecanyloxy, nonadecanyloxy and eicosanyloxy.

The term "alkyl" denotes a straight-chain or branched alkyl group having 1 to 20 C atoms, as described above, which may be partially or fully substituted by halogen, i.e. in the case of a perfluorinated alkyl group all H atoms of this alkyl group have been replaced by F. In the case of a partially fluorinated alkyl group, at least one H atom, but not all H atoms, has been replaced by an F atom (F atoms).

Preferred examples of a partially fluorinated straight-chain or branched alkyl group are $CF_3$—CHF—$CF_2$—, $CF_2H$—$CF_2$—, $CF_3$—$CF_2$—$CH_2$—, $CF_3$—$CF_2$—$CH_2$—$CH_2$—, or $CF_3$—$CF_2$—$CF_2$—$CF_2$—$CF_2$—$CH_2$—$CH_2$—.

A straight-chain or branched perfluoroalkyl group having 1 to 8 C atoms is, for example, trifluoromethyl, pentafluoroethyl, heptafluoropropyl, heptafluoroisopropyl, n-nonafluorobutyl, sec-nonafluorobutyl, tert-nonafluorobutyl, dodecafluoropentyl, 1-, 2- or 3-trifluoromethyloctafluorobutyl, 1,1-, 1,2- or 2,2-bis(trifluoromethyl)pentafluoropropyl, 1-pentafluoroethylhexafluoropropyl, n-tridecafluorohexyl, n-pentadecafluoroheptyl or n-heptadecafluorooctyl. Preferred examples of the perfluorinated alkyl group $R_f$ are pentafluoroethyl, heptafluoropropyl, heptafluoroisopropyl, n-nonafluorobutyl, sec-nonafluorobutyl or tert-nonafluorobutyl.

The term "cycloalkyl" denotes a cyclic saturated or partially unsaturated cycloalkyl group having 3 to 7 C atoms. Unsubstituted saturated or partially unsaturated cycloalkyl groups having 3-7 C atoms are therefore cyclopropyl, cyclobutyl, cyclopentyl, cyclohexyl, cycloheptyl, cyclopentenyl, cyclohexenyl or cycloheptenyl.

The term "Hal" denotes F, Cl, Br or I. Hal is preferably F, Cl or Br.

The term "aryl" denotes an aryl group having 6 or 10 C atoms, which may be mono- or polysubstituted by alkyl, O-alkyl, N(alkyl)$_2$ or Hal, for example phenyl or naphthyl, each of which is mono- or polysubstituted by alkyl, O-alkyl, N(alkyl)$_2$ or Hal, where alkyl and Hal have one of the meanings indicated above.

The term "Het" denotes O, S, N, —N=N—, NH or NR, where R has a meaning as described above and below. Het is preferably O, N or NR, where R denotes alkyl. Het is particularly preferably N.

A straight-chain or branched alkenyl having 2 to 20 C atoms, where a plurality of double bonds may also be present, is, for example, allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{20}H_{39}$; preferably allyl, 2- or 3-butenyl, isobutenyl, sec-butenyl, 4-pentenyl, isopentenyl, hexenyl or decenyl.

A straight-chain or branched alkynyl having 2 to 20 C atoms, where a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$, preferably ethynyl, 1- or 2-propynyl, 2- or 3-butynyl, 4-pentynyl, 3-pentynyl or hexynyl, where one or more double bonds may optionally be present. The straight-chain or branched alkynyl having 2 to 20 C atoms preferably contains one triple bond.

In the compounds of the formula I, $R^1$, $R^2$, $R^3$ and $R^4$ are each, independently of one another, preferably H, a straight-chain or branched alkyl group having 1 to 20 C atoms or a straight-chain or branched alkkoxy group having 1 to 20 C atoms.

In an embodiment, it is preferred if three of the substituents $R^1$, $R^2$, $R^3$ or $R^4$ denote H and one of the substituents $R^1$, $R^2$, $R^3$ or $R^4$ denotes NO$_2$, Hal, a straight-chain or branched alkyl group having 1 to 20 C atoms or a straight-chain or branched alkkoxy group having 1 to 20 C atoms, or preferably denotes a straight-chain or branched alkyl group having 1 to 20 C atoms or a straight-chain or branched alkkoxy group having 1 to 20 C atoms.

It is particularly preferred if $R^1$, $R^3$ and $R^4$ denote H.

It is particularly preferred if $R^2$ denotes a straight-chain or branched alkyl group having 1 to 8 C atoms, preferably methyl, ethyl, n-propyl, isopropyl, n-butyl, n-pentyl, n-hexyl, ethylhexyl or n-octyl. It is very particularly preferred if $R^2$ denotes methyl.

In the compounds of the formula I, X and Y each stand, independently of one another, for an aryl group or heteroaryl group having 5 to 24 ring atoms which is unsubstituted or mono- or polysubstituted by R, or a group of aryl and/or heteroaryl groups having 5 to 24 ring atoms which are unsubstituted or mono- or polysubstituted by R, where the aryl and/or heteroaryl groups in this group are each linked, independently of one another, singly or multiply, by a single bond, a double bond, conjugated double bonds, a C atom or by a unit of the formula —(CHR$^5$)$_n$-(Het)$_o$—(CHR$^5$)$_p$—, where R and R$^5$ have a meaning described above or below, n denotes an integer from 0 to 5, o denotes 0 or 1, p denotes an integer from 0 to 5 and the sum n+o+p denotes at least the number 1.

The aryl group having 6 to 24 ring atoms for the substituents X and/or Y in the sense of this invention is an aromatic group having a common aromatic electron system having 6 to 24 C atoms, optionally mono- or polysubstituted by R. The aryl group having 6 to 24 C atoms is preferably 1-, 2-, 3-, 4-, 5- or 6-phenyl, 1-, 2-, 3-, 4-, 6-, 7- or 8-naphthyl, 1-, 2-, 3-, 4-, 6-, 7- or 8-phenanthrenyl, 1-, 2-, 3-, 4-, 5-, 6-, 7-, 8-, 9- or 10-anthracenyl, 1-, 2-, 3-, 4-, 5-, 6-, 7-, 8-, 9-, 10-, 11- or 12-tetracenyl, 1-, 2-, 3-, 4-, 5-, 6-, 7-, 8-, 9-, 10-, 11- or 12-benzo[a]anthracenyl, 1-, 2-, 3-, 4-, 5-, 6-, 7-, 8-, 9-, 10-, 11-, 12-, 13- or 15-pentacenyl, 1-, 2-, 3-, 4-, 5-, 6-, 7-, 8-, 9-, 10-, 11- or 12-chrysenyl, 1-, 2-, 3-, 4-, 5-, 6-, 7-, 8-, 9- or 10-pyrenyl, 1-, 2-, 3-, 4-, 5-, 6-, 7-, 8-, 9-, 10-, 11- or 12-benzo[a]pyrenyl, 1-, 2-, 3-, 4-, 5-, 6-, 7- or 8-azulenyl, 1-, 2-, 3-, 4-, 5-, 6-, 7-, 8-, 9- or 10-fluoranthenyl, 1-, 2-, 3-, 4-, 5-, 6-, 7-, 8-, 9-, 10-, 11- or 12-perylenyl, 1-, 2-, 3-, 4-, 5-, 6- or 7-indenyl or 1-, 2-, 3-, 4-, 5-, 6-, 7-, 8- or 9-fluorenyl, each of which is substituted by R or unsubstituted.

The heteroaryl group having 5 to 24 ring atoms for the substituents X and/or Y is in the sense of this invention is a heteroaromatic group having a common aromatic electron system having 2 to 23 C atoms and in total at least 5 aromatic ring atoms, optionally mono- or polysubstituted by R. The heteroatoms are preferably selected from N, O and/or S. The heteroaryl group having 5 to 24 ring atoms is preferably 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 3-, 4-, 5-, 6- or 7-2H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl, 1-, 2-, 3-, 4-, 6-, 7-, 8- or 9-dibenzofuranyl, 1-, 2-, 3-, 4-, 6-, 7-, 8- or 9-dibenzothienyl, 1-, 2-, 3-, 5-, 6-, 7- or 8-indolizinyl, 1-, 2-, 3-, 4-, 6-, 7-, 8- or 10-phenanthridinyl 7-1H-indolyl, 1-, 2-, 3-, 4-, 6-, 7-, 8-, 9-, 10-, 11- or 12-benzophenanthridinyl or 1-, 2-, 3-, 4-, 6-, 7-, 8-, 9-, 10-, 11- or 12-benzoacridinyl, each of which is substituted by R or unsubstituted.

Examples of the unsubstituted basic structures which form the basis for the group of unsubstituted aryl and/or heteroaryl groups having 5 to 24 ring atoms, as described above, where the aryl and/or heteroaryl groups in this group are each linked, independently of one another, singly or multiply, by a single bond, a double bond, conjugated double bonds, a C atom or by a unit of the formula —(CHR$^5$)$_n$-(Het)$_o$—(CHR$^5$)$_p$— and R$^5$, n, o, p and n+o+p have a meaning described above or below, are biphenyl, terphenyl, bipyridine, 9,9'-spirobifluorene, 9,9-diphenylfluorene, diphenyl ether, diphenyl thioether, stilbene, 1,2-diphenylethane, 1,1-diphenylmethane, biphenylene, triphenylene, each of which may optionally be mono- or polysubstituted by R, as described above or below. The aryl and/or heteroaryl groups are preferably linked by a single bond.

n is denotes an integer from 0 to 5, in particular 0, 1, 2, 3 or 4, particularly preferably 0 or 1.

denotes 0 or 1. p denotes 0 to 5, in particular 0 or 1, and the sum n+o+p preferably denotes the number 1.

Further more-complex unsubstituted basic structures for the above-described group of unsubstituted aryl and/or heteroaryl groups having 5 to 24 ring atoms, where the aryl and/or heteroaryl groups are linked to one another by the alternatives indicated, as described above, can be represented by the following formulae:

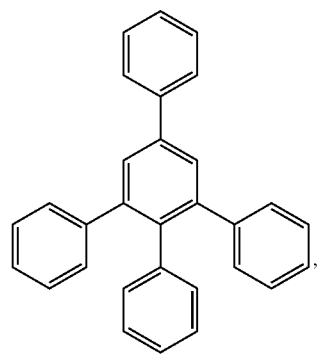 [SMILES: c1ccc(-c2cc(-c3ccccc3)c(-c3ccccc3)c(-c3ccccc3)c2)cc1]

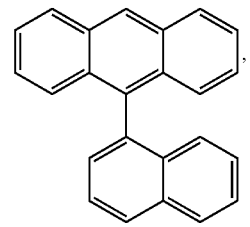 [SMILES: c1ccc2c(-c3c4ccccc4cc4ccccc34)cccc2c1]

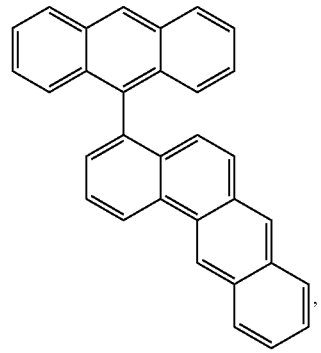 [SMILES: c1ccc2cc3c(ccc4c(-c5c6ccccc6cc6ccccc56)cccc43)cc2c1]

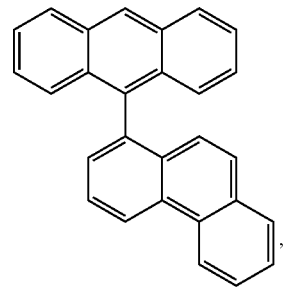 [SMILES: c1ccc2c(-c3cccc4c3ccc3ccccc34)c3ccccc3cc2c1]

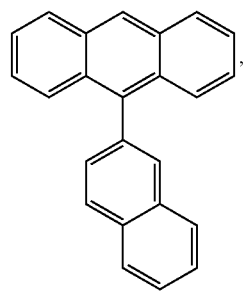 [SMILES: c1ccc2cc(-c3c4ccccc4cc4ccccc34)ccc2c1]
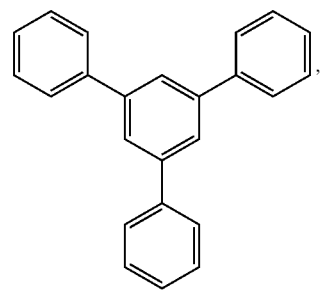
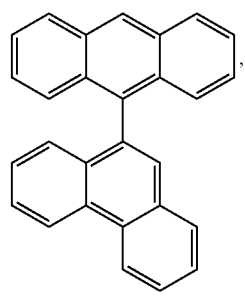 [SMILES: c1ccc2c(-c3cc4ccccc4c4ccccc34)c3ccccc3cc2c1]
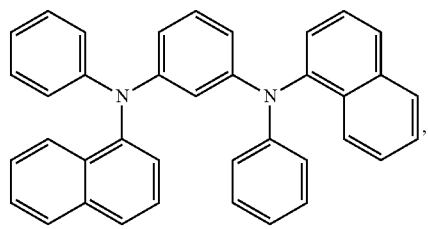
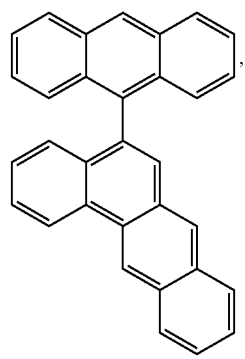 [SMILES: c1ccc2cc3c(cc(-c4c5ccccc5cc5ccccc45)c4ccccc43)cc2c1]
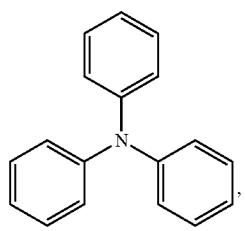 [SMILES: c1ccc(N(c2ccccc2)c2ccccc2)cc1]
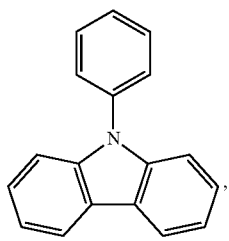 [SMILES: c1ccc(-n2c3ccccc3c3ccccc32)cc1]
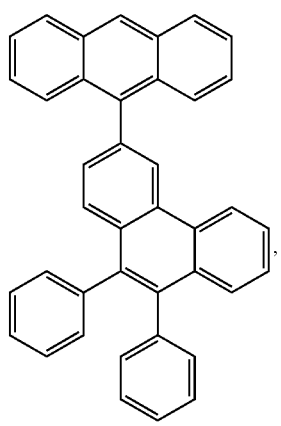
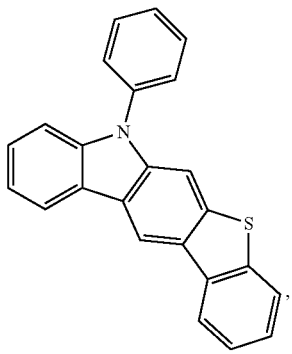 [SMILES: c1ccc(-n2c3ccccc3c3cc4c(cc32)sc2ccccc24)cc1]

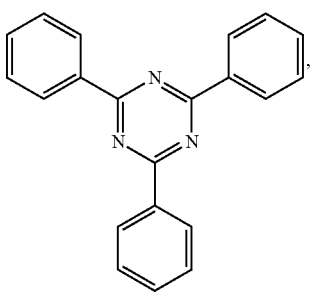 [SMILES: c1ccc(-c2nc(-c3ccccc3)nc(-c3ccccc3)n2)cc1]

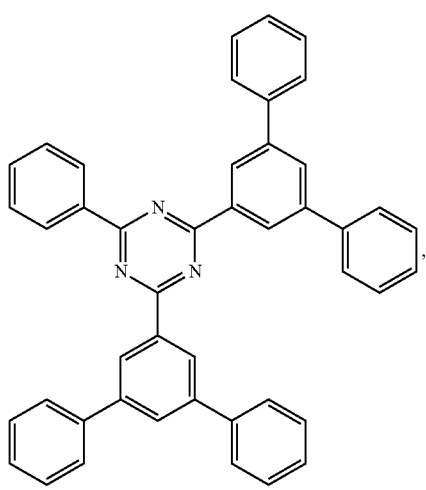 [SMILES: c1ccc(-c2cc(-c3ccccc3)cc(-c3nc(-c4ccccc4)nc(-c4cc(-c5ccccc5)cc(-c5ccccc5)c4)n3)c2)cc1]

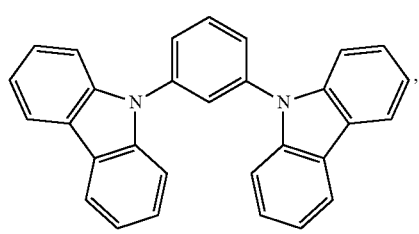 [SMILES: c1cc(-n2c3ccccc3c3ccccc32)cc(-n2c3ccccc3c3ccccc32)c1]

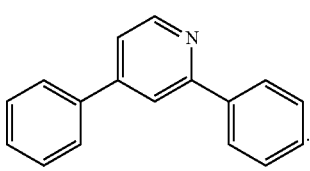 [SMILES: c1ccc(-c2ccnc(-c3ccccc3)c2)cc1]

R in each case, independently of one another on each occurrence, denotes D, Hal, alkyl, OH, O-alkyl, O-aryl, S-alkyl, $NH_2$, NHalkyl, $N(alkyl)_2$, $N(aryl)_2$, cycloalkyl, O-cycloalkyl, S-cycloalkyl, NH-cycloalkyl, $N(cycloalkyl)_2$, CN, $NO_2$, $Si(alkyl)_3$, $B(OR^6)_2$, $C(O)R^6$, $P(O)(R^6)_2$, $S(O)R^6$, $S(O)_2R^6$, a straight-chain or branched alkenyl group having 2 to 20 C atoms and one or more double bonds or a straight-chain or branched alkynyl group having 2 to 20 C atoms and at least one triple bond and optionally one or more double bonds, where Hal, alkyl, aryl and cycloalkyl have a meaning given above and $R^6$ in each case, independently of one another, denotes H, D, OH, alkyl, aryl, cycloalkyl, O-alkyl, O-aryl or O-cycloalkyl.

$R^6$ is preferably H or alkyl, where alkyl has a meaning as described above.

R is in each case, independently of one another, preferably Hal, alkyl, O-alkyl, O-aryl, NHalkyl, $N(alkyl)_2$. Compounds of the formula I in which X and/or Y are substituted by this preferred group of R are preferably employed as dyes or for the protection of skin and hair against photoageing.

Alkyl in the definition of R is preferably a straight-chain or branched alkyl group having 1 to 8 C atoms, which may optionally also be partially fluorinated. Particularly preferred substituents R are methyl, isopropyl, trifluoromethyl, methoxy, di-(n-butyl)amino, dimethylamino, n-octyloxy, phenyloxy, —F or —Br.

$R^5$ in each case, independently of one another on each occurrence, denotes H, D, Hal, alkyl, OH, O-alkyl, O-aryl, S-alkyl, $NH_2$, NHalkyl, $N(alkyl)_2$, $N(aryl)_2$, cycloalkyl, O-cycloalkyl, S-cycloalkyl, NH-cycloalkyl, $N(cycloalkyl)_2$, CN, $NO_2$, $Si(alkyl)_3$, $B(OR^6)_2$, $C(O)R^6$, $P(O)(R^6)_2$, $S(O)R^6$, $S(O)_2R^6$, a straight-chain or branched alkenyl group having 2 to 20 C atoms and one or more double bonds or a straight-chain or branched alkynyl group having 2 to 20 C atoms and at least one triple bond and optionally one or more double bonds, where $R^6$, Hal, alkyl, aryl and cycloalkyl have a meaning given above. $R^5$ is preferably H, Hal or alkyl, very particularly preferably H. Alkyl in the definition of $R^5$ is preferably a straight-chain or branched alkyl group having 1 to 8 C atoms, which may optionally also be partially fluorinated.

If the focus of the application is on the use as fluorescent emitter, it may be preferred for X and/or Y to be unsubstituted or mono- or polysubstituted by R, where R denotes alkyl and alkyl preferably denotes a straight-chain or branched alkyl group having 1 to 4 C atoms.

If the focus of the application is on the use as fluorescent emitter, a group of aryl and/or heteroaryl groups having 5 to 24 ring atoms which are unsubstituted or mono- or polysubstituted by R, where the aryl and/or heteroaryl groups in this group are each linked, independently of one another, singly or multiply, by a single bond or an O atom, are preferably selected, in each case independently of one another, for X and Y, where R denotes alkyl and alkyl preferably denotes a straight-chain or branched alkyl group having 1 to 4 C atoms, in particular biphenyl, terphenyl or the groups of the formula

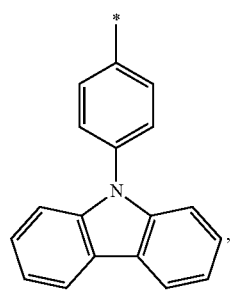 [SMILES: *c1ccc(-n2c3ccccc3c3ccccc32)cc1]

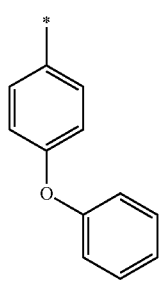 [SMILES: *c1ccc(Oc2ccccc2)cc1]

or

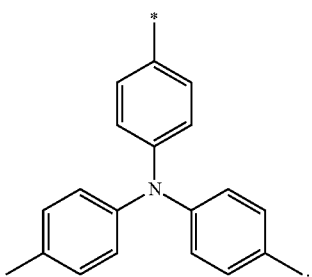

X and Y are preferably each, independently of one another, an aryl or heteroaryl group having 5 to 24 ring atoms which is unsubstituted or mono- or polysubstituted by R.

If the focus of the application is on the use as dye or for the protection of skin and hair against photoageing, in particular on the further use as constituent of cosmetic, pharmaceutical, dermatological preparations or household products, aryl or heteroaryl groups, from the group phenyl, naphthyl, anthracenyl, indolyl, 9-carbazol-4-yl, azulenyl, fluorenyl, thienyl, quinolinyl, dibenzopyrrolyl, which are unsubstituted or mono- or polysubstituted by R are preferably selected, in each case independently of one another, for X and Y.

Aryl or heteroaryl groups from the group phenyl, naphthyl, azulenyl, indolyl or thienyl which are unsubstituted or mono- or polysubstituted by R are particularly preferably employed for use as dye or for the protection of skin and hair against photoageing.

In the case of the compounds of the formula I, it is particularly preferred for X and Y to be identical.

Preferred individual compounds of the formula I and double-bond isomers and photoisomers thereof or very particularly preferred individual compounds of the formula I are 2,4-bis[1-(4-methoxyphenyl)meth-(Z)-ylidene]-7-methylbenzo[b]-1,4-dioxepin-3-one,
2,4-bis[1-(3,4-dimethoxyphenyl)meth-(Z)-ylidene]-7-methylbenzo[b]-1,4-dioxepin-3-one,
2,4-bis[1-(2,4-dimethoxyphenyl)meth-(Z)-ylidene]-7-methylbenzo[b]-1,4-dioxepin-3-one,
7-methyl-2,4-bis[1-(2,4,5-trimethoxyphenyl)meth-(Z)-ylidene]benzo[b]-1,4-dioxepin-3-one,
7-methyl-2,4-bis[1-(3,4,5-trimethoxyphenyl)meth-(Z)-ylidene]benzo[b]-1,4-dioxepin-3-one,
7-methyl-2,4-bis[1-(4-octyloxyphenyl)meth-(Z)-ylidene]benzo[b]-1,4-dioxepin-3-one,
7-methyl-2,4-bis[1-(4-phenoxyphenyl)meth-(Z)-ylidene]benzo[b]-1,4-dioxepin-3-one,
7-methyl-2,4-bis[1-(4-dibutylaminophenyl)meth-(Z)-ylidene]benzo[b]-1,4-dioxepin-3-one,
2,4-bis[1-(4-fluorophenyl)meth-(Z)-ylidene]-7-methylbenzo[b]-1,4-dioxepin-3-one,
7-methyl-2,4-bis[1-(4-trifluoromethylphenyl)meth-(Z)-ylidene]benzo[b]-1,4-dioxepin-3-one,
7-methyl-2,4-bis[1-(2,4,6-trimethoxyphenyl)meth-(Z)-ylidene]benzo[b]-1,4-dioxepin-3-one,
7-methyl-2,4-bis[1-(2,3,4-trimethoxyphenyl)meth-(Z)-ylidene]benzo[b]-1,4-dioxepin-3-one,
2,4-bis[1-biphenyl-4-ylmeth-(Z)-ylidene]-7-methylbenzo[b]-1,4-diosepin-3-one,
7-methyl-2,4-bis[1-naphthalen-1-ylmeth-(Z)-ylidene]benzo[b]-1,4-dioxepin-3-one,
7-methyl-2,4-bis[1-(1-methyl-1H-indol-3-yl)meth-(Z)-ylidene]benzo[b]-1,4-dioxepin-3-one,
7-methyl-4-[1-(9-ethyl-9H-carbazol-3-yl)meth-(Z)-ylidene]benzo[b]-1,4-dioxepin-3-one,
2,4-bis[1-(4-dimethylamino-2-methoxyphenyl)meth-(Z)-ylidene]-7-methylbenzo[b]-1,4-dioxepin-3-one,
2,4-bis[1-(4-dimethylaminonaphthalen-1-yl)meth-(Z)-ylidene]-7-methylbenzo[b]-1,4-dioxepin-3-one,
2,4-bis[1-(4-bromophenyl)meth-(Z)-ylidene]-7-methylbenzo[b]-1,4-dioxepin-3-one,
7-methyl-2,4-bis[1-thiophen-2-ylmeth-(Z)-ylidene]benzo[b]-1,4-dioxepin-3-one,
4-[1-(4-dibutylaminophenyl)meth-(Z)-ylidene]-2-[1-(4-methoxyphenyl)meth-(Z)-ylidene]-7-methylbenzo[b]-1,4-dioxepin-3-one,
2,4-bis[1-(5-isopropyl-3,8-dimethylazulen-1-yl)meth-(Z)-ylidene]-7-methylbenzo[b]-1,4-dioxepin-3-one,
2,4-bis[1-(4-carbazolyl-9-ylphenyl)meth-(Z)-ylidene]-7-methylbenzo[b]-1,4-dioxepin-3-one,
7-methyl-2,4-bis[1-[1,1';3',1"]terphenyl-2'-ylmeth-(Z)-ylidene]benzo[b]-1,4-dioxepin-3-one, and
2,4-bis[1-[4-(di-p-tolylamino)phenyl]meth-(Z)-ylidene]-7-methylbenzo[b]-1,4-dioxepin-3-one.

The compounds of the formula I according to the invention, as described or described as preferred above, have very good solubilities and dispersibilities, in particular in relatively lipophilic, non-aqueous solvents and solvent mixtures. The dyes of the formula I are therefore lipophilic. The colours are distinguished by high light fastness, heat and pH stability, and by high colour intensities and intense fluorescence properties. The compounds of the formula I are themselves likewise light-fast and thermostable. A further advantage of the compounds of the formula I is their high substantivity to surfaces, in particular to keratin-containing surfaces, such as skin, hair or nails. Examples of further dyeable surfaces or substrates include paper, cotton, wool, plastics, for example based on polyethylene, polypropylene, polyurethane, polyamide, cellulose or glass, where the dye can either be added during substrate production or the substrate can be dyed subsequently.

The invention therefore furthermore relates to the use of the compounds of the formula I, as described or described as preferred above, as dye.

The lipophilicity of the compounds of the formula I can be varied by introducing further substituents R which are hydrophilic, for example COOH groups, $SO_3H$ groups or corresponding salt-forming groups thereof, for example —COOKt, —$SO_3$Kt, where the cation Kt is preferably an ammonium ion or an alkali metal or alkaline-earth metal cation, such as $Na^+$, $K^+$, $Mg^{2+}$ or $Ca^{2+}$.

The dyes are particularly suitable for the dyeing of skin, hair or for the colouring of cosmetic, pharmaceutical or dermatological preparations or household products.

A further preferred use of the compounds of the formula I is protection of skin and hair against photoageing by visible light. The scientific knowledge in this respect is described, for example, in Zastrow et al, Skin Pharmacol. Physiol 2009, 22, 31-44. For this reason, it is particularly preferred to combine with known UVB and UVA filters in preparations in order to generate a broad-band protection system that in the ideal case can cover the entire UV and V is region.

The invention therefore furthermore relates to the use of the compounds of the formula I, as described or described as preferred above, for the protection of the skin and hair against photoageing by light, in particular by visible light.

The invention also relates to a process for the preparation of the compounds of the formula I,

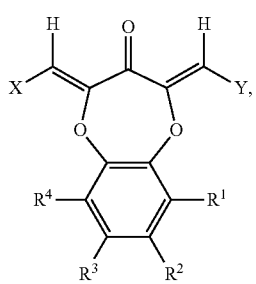

I where $R^1$, $R^2$, $R^3$ and $R^4$ each, independently of one another, denote H, $NO_2$, Hal, a straight-chain or branched alkyl group having 1 to 20 C atoms or a straight-chain or branched alkoxy group having 1 to 20 C atoms, X and Y each, independently of one another, denote an aryl or heteroaryl group having 5 to 24 ring atoms which is unsubstituted or mono- or polysubstituted by R, or a group of aryl and/or heteroaryl groups having 5 to 24 ring atoms which are unsubstituted or mono- or polysubstituted by R, where the aryl and/or heteroaryl groups in this group are each linked, independently of one another, singly or multiply, by a single bond, a double bond, conjugated double bonds, a C atom or by a unit of the formula $(CHR^5)_n$-$(Het)_o$—$(CHR^5)_p$, R in each case, independently of one another on each occurrence, denotes D, Hal, alkyl, OH, O-alkyl, O-aryl, S-alkyl, $NH_2$, NHalkyl, $N(alkyl)_2$, $N(aryl)_2$, cycloalkyl, O-cycloalkyl, S-cycloalkyl, NH-cycloalkyl, $N(cycloalkyl)_2$, CN, $NO_2$, $Si(alkyl)_3$, $B(OR^6)_2$, $C(O)R^6$, $P(O)(R^6)_2$, $S(O)R^6$, $S(O)_2R^6$, a straight-chain or branched alkenyl group having 2 to 20 C atoms and one or more double bonds or a straight-chain or branched alkynyl group having 2 to 20 C atoms and at least one triple bond and optionally one or more double bonds, $R^5$ in each case, independently of one another on each occurrence, denotes H, D, Hal, alkyl, OH, O-alkyl, O-aryl, S-alkyl, $NH_2$, NHalkyl, $N(alkyl)_2$, $N(aryl)_2$, cycloalkyl, O-cycloalkyl, S-cycloalkyl, NH-cycloalkyl, $N(cycloalkyl)_2$, CN, $NO_2$, $Si(alkyl)_3$, $B(OR^6)_2$, $C(O)R^6$, $C(O)_2R^6$, $P(O)(R^6)_2$, $S(O)R^6$, $S(O)_2R^6$, a straight-chain or branched alkenyl group having 2 to 20 C atoms and one or more double bonds or a straight-chain or branched alkynyl group having 2 to 20 C atoms and at least one triple bond and optionally one or more double bonds, $R^6$ in each case, independently of one another, denotes H, D, OH, alkyl, aryl, cycloalkyl, Oalkyl, Oaryl or O-cycloalkyl, alkyl denotes a straight-chain or branched alkyl group having 1 to 20 C atoms, which may be partially or fully substituted by halogen, cycloalkyl denotes a cyclic saturated or partially unsaturated cycloalkyl group having 3 to 7 C atoms, aryl denotes an aryl group having 6 to 10 C atoms, which may be mono- or polysubstituted by alkyl, Oalkyl, $N(alkyl)_2$ or Hal, Hal denotes F, Cl, Br or I, Het denotes O, S, —N=N—, NH or NR, n denotes an integer from 0 to 5, o denotes 0 or 1, p denotes an integer from 0 to 5, n+o+p denotes at least the number 1, characterised in that a compound of the formula II

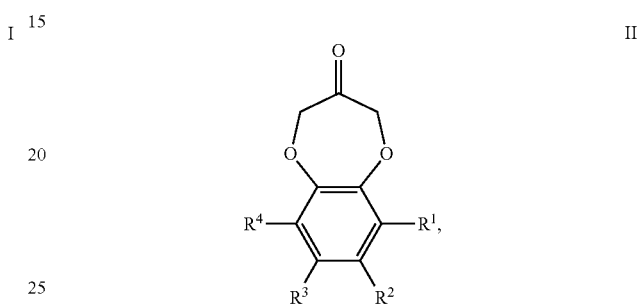

II where $R^1$, $R^2$, $R^3$ and $R^4$ have a meaning given or given as preferred above, is reacted with a compound of the formula IIIa and/or IIIb

IIIa

IIIb where X and Y have a meaning given or given as preferred above.

The said reaction of the compounds of the formula II with at least one compound of the formula IIIa or IIIb is generally carried out in accordance with conditions of the Michael addition, which is known to the person skilled in the art in the area of synthetic chemistry. The reaction generally requires the presence of a strong base, for example alkali metal hydroxides, such as sodium hydroxide or potassium hydroxide, or strong organic bases, such as lithium diisopropylamide. Preference is given to the use of alkali metal hydroxides. The at least one aldehyde of the formula IIIa or IIIb is generally employed in excess, but at least with one equivalent in relation to the compound of the formula II. If it is desired to prepare asymmetrical compounds of the formula I, a mixture of 2 aldehydes of the formula IIIa and/or IIIb is added. If the reaction kinetics of the two aldehydes differ greatly, the corresponding aldehydes of the formulae IIIa and/or IIIb can be metered in individually in accordance with their kinetics.

Separation of any mixtures of compounds of the formula I that possibly form to give isolated compounds of the formula I is possible using conventional methods.

The process indicated above is preferably carried out at temperatures between 0° C. and 150° C., particularly preferably at temperatures between 30° C. and the boiling point of the solvent used. Suitable solvents for the said reaction are alcohols, such as, for example, methanol, ethanol, butanol, and other organic solvents, such as dioxane, tert-butyl methyl ether, dichloromethane, chloroform and toluene. The reaction is preferably carried out in ethanol.

The compounds of the formula II, as described above, are commercially available or can be prepared on the basis of the publication EP 1405851. In general, 1,3-dichloroacetone, sodium carbonate as base, potassium iodide as catalyst and catechol in ethyl methyl ketone is reacted under reflux.

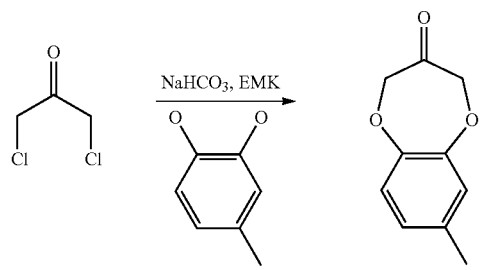

The use of other catechols also enables other compounds of the formula II to be synthesised The aldehydes of the formula IIIa or IIIb are generally commercially available or can be prepared by known methods.

The compounds of the formula I, prepared by the process outlined above, can be purified by a very wide variety of purification methods which are adequately known to the person skilled in the art, for example by chromatography, distillation or recrystallisation.

The conversion into salts of the compounds of the formula I is carried out, for example, by addition of an alkali or alkaline-earth metal hydroxide, carbonate or bicarbonate in a polar solvent, for example in ethanol, methanol or isopropanol, if the compounds of the formula I carry substituents R which can be converted into a salt, for example COOH or $SO_3H$ groups.

The compounds of the formula I according to the invention described above, which carry, in particular, substituents R selected from the group Hal or $B(OR^6)_2$, can be used, for example, as comonomers for the production of corresponding conjugated, partially conjugated or non-conjugated polymers, oligomers or also as core of dendrimers. The polymerisation here is preferably carried out via the halogen functionality. Substituents R which are preferred for this further conversion are Cl, Br, I, $B(OH)_2$ or corresponding boric acid esters $B(Oalkyl)_2$, where alkyl preferably denotes a straight-chain or branched alkyl group having 1 to 4 C atoms, very particularly preferably $B(Omethyl)_2$.

The invention thus furthermore relates to conjugated, partially conjugated and non-conjugated polymers, oligomers or dendrimers containing one or more compounds of the formula I, where the linking site between the at least one compound of the formula I and the polymer, oligomer or dendrimer is at the position at which the at least one radical R of the compound of the formula I was located before the reaction.

These polymers may contain further recurring units. These further recurring units are preferably selected from the group consisting of fluorenes (for example in accordance with EP 842208 or WO 00/22026), spirobifluorenes (for example in accordance with EP 707020, EP 894107 or EP 04028865.6), triarylamines, para-phenylenes (for example in accordance with WO 92/18552), carbazoles (for example in accordance with WO 04/070772 and WO 04/113468), thiophenes (for example in accordance with EP 1028136), dihydrophenanthrenes (for example in accordance with WO 05/014689), indenofluorenes (for example in accordance with WO 04/041901 and WO 04/113412), aromatic ketones (for example in accordance with WO 05/040302), phenanthrenes (for example in accordance with WO 05/104264) and/or metal complexes, in particular ortho-metallated iridium complexes. It should be expressly pointed out here that the polymers may also contain a plurality of different recurring units selected from one or more of the above-mentioned groups.

The present invention furthermore relates to a preparation comprising at least one compound of the formula I.

In the sense of the present invention, the term composition or formulation is also used synonymously alongside the term preparation.

The preparation may include or comprise, essentially consist of or consist of the said necessary or optional constituents. All compounds or components which can be used in the preparations are either known and commercially available or can be synthesised by known processes.

In addition to the at least one compound of the formula I, the preparation here may comprise a vehicle which is suitable for cosmetic, pharmaceutical, dermatological preparations or household products. Suitable vehicle materials are described below.

The invention also relates to a process for the preparation of a preparation of this type, characterised in that the at least one compound of the formula I is mixed, in particular dispersed and/or emulsified and/or dissolved, with at least one vehicle which is suitable for cosmetic, pharmaceutical, dermatological preparations or household products and optionally assistants and/or fillers.

Suitable assistants or fillers are described below.

The compounds of the formula I are dyes which are suitable for the dyeing of the skin or hair and may therefore also be a constituent of colorants.

The compounds of the formula I, as described or described as preferred above, can, in a preferred application, be employed in compositions for the dyeing of keratin-containing fibres, in particular for the dyeing of human hair, which are selected, for example, from a coloured setting composition, a coloured blow-dry lotion, a coloured blow-dry foam, a coloured rinse, a coloured gel or a coloured cream. However, they may also be present in compositions for permanent hair dyeing, for example in multicomponent systems.

Keratin-containing fibres are preferably taken to mean human hair, wool, pelts or feathers. However, the compounds according to the invention are in principle also suitable for the dyeing of other natural fibres, such as, for example, cotton, jute, sisal, linen or silk, or for the dyeing of modified natural fibres, such as, for example, regenerated cellulose, nitro-, alkyl- or hydroxyalkyl- or acetylcellulose. The keratin-containing fibre is particularly preferably human hair.

The corresponding compositions for the dyeing of keratin-containing fibres, as described above, preferably comprise the compound(s) of the formula I in amounts above 0.01% by weight and below 10% by weight, in each case based on the entire composition. Preferred compositions for the dyeing of keratin-containing fibres are characterised in that they comprise the compound(s) of the formula I in amounts of 0.05 to 5% by weight, preferably 0.1 to 2.5% by weight, particularly preferably 0.25 to 1.5% by weight and in particular 0.4 to 1% by weight, in each case based on the entire composition.

The corresponding compositions comprising at least one compound of the formula I serve for changing the colour of keratin-containing fibres, as described above, in particular human hair. The colour change can take place solely owing to the compound(s) of the formula I, but the compositions may also additionally comprise further colour-changing substances, for example further direct dyes and/or oxidation colorants.

The composition for the dyeing of keratin-containing fibres comprising at least one compound of the formula I, as described above, can be formulated as a single-component composition, as a two-component composition or as a three-component composition and used correspondingly. Separation in multicomponent systems is appropriate, in particular, where incompatibilities of the ingredients are to be expected or feared. In the case of such systems, the composition to be employed is prepared by the consumer immediately before application by mixing the components.

The invention furthermore relates to a method for the dyeing of keratin-containing fibres, in which a composition for the dyeing of keratin-containing fibres comprising at least one compound of the formula I, as described or described as preferred above, is applied to the keratin-containing fibre at least once daily or at least twice or a number of times successively, left on the fibre for some time, usually about 20 to 45 minutes, and subsequently rinsed out again or washed out using a shampoo.

However, it is also possible to carry out a pretreatment of the keratin-containing fibres and then to apply the composition comprising the at least one compound of the formula I.

Furthermore, in order, for example, to be able to carry out further colour adaptations, the compositions comprising the at least one compound of the formula I may comprise further oxidation dye components.

Coupler components generally allow at least one substitution of a chemical radical of the coupler by the oxidised form of the developer component. A covalent bond forms here between coupler and developer component. Couplers are preferably cyclic compounds which carry at least two groups on the ring, selected from (i) optionally substituted amino groups and/or (ii) hydroxyl groups. These groups are in conjugation through a double-bond system. If the cyclic compound is a six-membered ring, the said groups are preferably located in the ortho-position or meta-position to one another.

Developer components and coupler components are generally employed here in approximately molar amounts to one another. If the molar use has also proven advantageous, a certain excess of individual oxidation dye precursors is not disadvantageous, meaning that developer components and coupler components can be in a molar ratio of 1:0.5 to 1:3, in particular 1:1 to 1:2.

Suitable oxidation dye components of the developer type are p-phenylenediamine and derivatives thereof. Suitable p-phenylenediamines are selected from one or more compounds from the group formed by p-phenylenediamine, p-toluoylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis(2-hydroxyethyl)-p-phenylenediamine, 4-N,N-bis(2-hydroxyethyl)amino-2-methylaniline, 4-N,N-bis(2-hydroxyethyl)amino-2-chloroaniline, 2-(2-hydroxyethyl)-p-phenylenediamine, 2-(1,2-dihydroxyethyl)-p-phenylenediamine, 2-fluoro-p-phenylenediamine, 2-isopropyl-p-phenylenediamine, N-(2-hydroxypropyl)-p-phenylenediamine, 2-hydroxymethyl-p-phenylenediamine, N,N-dimethyl-3-methyl-p-phenylenediamine, N-ethyl-N2-hydroxy-ethyl-p-phenylenediamine, N-(2,3-dihydroxypropyl)-p-phenylenediamine, N-(4'-aminophenyl)-p-phenylenediamine, N-phenyl-p-phenylenediamine, 2-(2-hydroxyethyloxy)-p-phenylenediamine, 2-methoxymethyl-p-phenylene-diamine, 2-(2-acetylaminoethyloxy)-p-phenylenediamine, N-(2-methoxy-ethyl)-p-phenylenediamine, N-(4-amino-3-methylphenyl)-N-[3-(1H-imidazol-1-yl)propyl]amine, 5,8-diaminobenzo-1,4-dioxane and physiologically tolerated salts thereof. Further suitable p-phenylenediamine derivatives are selected from at least one compound from the group p-phenylenediamine, p-toluoylenediamine, 2-(2-hydroxyethyl)-p-phenylenediamine, 2-(1,2-dihydroxyethyl)-p-phenylenediamine, N,N-bis(2-hydroxyethyl)-p-phenylene-diamine, N-(4-amino-3-methylphenyl)-N-[3-(1H-imidazol-1-yl)propyl]amine, 2-methoxymethyl-p-phenylenediamine and the physiologically tolerated salts of these compounds.

Further suitable developer components which can be employed are compounds which contain at least two aromatic rings which are substituted by amino and/or hydroxyl groups. Further suitable developer components are selected, in particular, from at least one compound from the group formed by N,N'-bis(2-hydroxyethyl)-N,N'-bis(4'-aminophenyl)-1,3-diaminopropan-2-ol, N,N'-bis(2-hydroxyethyl)-N,N'-bis(4'-aminophenyl)ethylenediamine, N,N'-bis(4'-aminophenyl)tetramethylenediamine, N,N'-bis(2-hydroxyethyl)-N,N'-bis(4'-aminophenyl)tetramethylenediamine, N,N'-bis(4-(methylamino)-phenyl)tetramethylenediamine, N,N'-diethyl-N,N'-bis(4'-amino-3'-methylphenyl) ethylenediamine, bis(2-hydroxy-5-aminophenyl)methane, N,N'-bis-(4'-aminophenyl)-1,4-diazacycloheptane, N,N'-bis(2-hydroxy-5-amino-benzyl)piperazine, N-(4'-aminophenyl)-p-phenylenediamine and 1,10-bis-(2',5'-diaminophenyl)-1,4,7,10-tetraoxadecane and physiologically tolerated salts thereof. Further suitable bicyclic developer components are selected from N,N'-bis(2-hydroxyethyl)-N,N'-bis(4-aminophenyl)-1,3-diaminopropan-2-ol, bis(2-hydroxy-5-aminophenyl)methane, 1,3-bis(2,5-diaminophenoxy)-propan-2-ol, N,N'-bis(4-aminophenyl)-1,4-diazacycloheptane, 1,10-bis(2,5-diaminophenyl)-1,4,7,10-tetraoxadecane or one of the physiologically tolerated salts of these compounds.

It may furthermore be possible to employ a p-aminophenol derivative or one of its physiologically tolerated salts as developer component. Preferred p-aminophenols are p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(2-hydroxyethoxy)-phenol, 4-amino-2-methylphenol, 4-amino-2-hydroxymethylphenol, 4-amino-2-methoxymethylphenol, 4-amino-2-aminomethylphenol, 4-amino-2-(2-hydroxyethylaminomethyl)phenol, 4-amino-2-(1,2-dihydroxyethyl)phenol, 4-amino-2-fluorophenol, 4-amino-2-chlorophenol, 4-amino-2,6-dichloro-phenol, 4-amino-2-(diethylaminomethyl)phenol and physiologically tolerated salts thereof. Particularly preferred compounds are p-aminophenol, 4-amino-3-methylphenol, 4-amino-2-aminomethylphenol, 4-amino-2-(1,2-dihydroxyethyl)phenol and 4-amino-2-(diethylaminomethyl)phenol.

Furthermore, the developer component can be selected from o-aminophenol and derivatives thereof, such as, for example, 2-amino-4-methylphenol, 2-amino-5-methylphenol or 2-amino-4-chlorophenol.

Furthermore, the developer component can be selected from heterocyclic developer components, such as, for example, from pyrimidine derivatives, pyrazole derivatives, pyrazolopyrimidine derivatives or physiologically tolerated salts thereof. Preferred pyrimidine derivatives are, in particular, the compounds 2,4,5,6-tetraminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine. Further suitable pyrazole derivatives are the compounds selected from 4,5-diamino-1-methylpyrazole, 4,5-diamino-1-(2-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenyl-pyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-t-butyl-1-methylpyrazole, 4,5-diamino-1-t-butyl-3-methylpyrazole, 4,5-diamino-1-(2-hydroxyethyl)-3-methylpyrazole, 4,5-diamino-1-ethyl-3-methylpyrazole, 4,5-diamino-1-ethyl-3-(4-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl)amino-1,3-dimethyl-pyrazole, and physiologically tolerated salts thereof, but in particular 4,5-diamino-1-(2-hydroxyethyl)pyrazole. Suitable pyrazolopyrimidines are, in particular, pyrazolo[1,5-a]pyrimidines, where preferred pyrazolo[1,5-a]-pyrimidines are selected from pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo-[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 3-amino-7-dimethylamino-2,5-dimethylpyrazolo[1,5-a]pyrimidine and physiologically tolerated salts thereof and tautomeric forms thereof.

Further suitable developer components are selected from at least one compound from the group formed by p-phenylenediamine, p-toluoylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,M-bis(2-hydroxyethyl)-N,N'-bis(4-aminophenyl)-1,3-diaminopropan-2-ol, bis(2-hydroxy-5-aminophenyl)methane, 1,3-bis(2,5-diaminophenoxy)propan-2-ol, N,N'-bis(4-aminophenyl)-1,4-diazacycloheptane, 1,10-bis(2,5-diaminophenyl)-1,4,7,10-tetraoxadecane, p-amino-phenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl) pyrazole, 2,4,5,6-tetraminopyrimidine, 4-hydroxy-2,5,6-triaminopyrimidine, 2-hydroxy-4,5,6-triaminopyrimidine, and the physiologically tolerated salts of these compounds. Further suitable developer components here are p-toluoylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole and physiologically tolerated salts thereof.

The developer components are preferably used in an amount of 0.0001 to 10% by weight, preferably 0.001 to 5% by weight, in each case based on the entire colorant.

Suitable oxidation dye components of the coupler type are preferably selected from m-aminophenol and/or derivatives thereof, m-diaminobenzene and/or derivatives thereof, o-diaminobenzene and/or derivatives thereof, o-aminophenol and/or derivatives thereof, naphthalene derivatives containing at least one hydroxyl group, di- or trihydroxybenzene and/or derivatives thereof, pyridine derivatives, pyrimidine derivatives, mono-hydroxyindole derivatives and/or monoaminoindole derivatives, mono-hydroxyindoline derivatives and/or monoaminoindoline derivatives, pyrazolone derivatives, such as, for example, 1-phenyl-3-methylpyrazol-5-one, morpholine derivatives, such as, for example, 6-hydroxybenzomorpholine or 6-aminobenzomorpholine, quinoxaline derivatives, such as, for example, 6-methyl-1,2,3,4-tetrahydroquinoxaline, and/or mixtures of two or more compounds from one or more of these classes.

Further coupler components which can be used, such as m-aminophenols or derivatives thereof, are preferably selected from at least one compound from the group formed by 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetyl-amino-2-chloro-6-methylphenol, 5-amino-4-chloro-2-methylphenol, 5-amino-4-methoxy-2-methylphenol, 5-(2'-hydroxyethyl)amino-2-methylphenol, 3-diethylaminophenol, N-cyclopentyl-3-aminophenol, 1,3-dihydroxy-5-(methylamitio)benzene, 3-ethylamino-4-methylphenol, 2,4-dichloro-3-aminophenol and physiologically tolerated salts thereof.

Further coupler components which can be used, such as, for example, 3-diaminobenzenes or derivatives thereof, are preferably selected from at least one compound from the group formed by m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diamino-phenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino) ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis(2'-hydroxyethyl)aminobenzene and physiologically tolerated salts thereof.

Further coupler components which can be used, such as, for example, o-diaminobenzenes or derivatives thereof, are preferably selected from at least one compound from the group formed by 3,4-diaminobenzoic acid and 2,3-diamino-1-methylbenzene and physiologically tolerated salts thereof. Further coupler components which can be used, such as, for example, di- or trihydroxybenzenes and derivatives thereof, are selected from at least one compound from the group formed by resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene.

Further coupler components which can be used, such as, for example, pyridine derivatives, are selected from at least one compound from the group formed by 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4- methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine and physiologically tolerated salts thereof.

Naphthalene derivatives containing at least one hydroxyl group which are suitable as coupler component are selected from at least one compound from the group formed by 1-naphthol, 2-methyl-1-naphthol, 2-hydroxy-methyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene.

Indole derivatives which are suitable as coupler component are selected from 4-hydroxyindole, 6-hydroxyindole and 7-hydroxyindole and physiologically tolerated salts thereof.

Indoline derivatives which are suitable as coupler component are preferably selected from 4-hydroxyindoline, 6-hydroxyindoline and 7-hydroxyindoline and physiologically tolerated salts thereof.

Pyrimidine derivatives which are suitable as coupler component are selected from at least one compound from the group formed by 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine and physiologically tolerated salts thereof.

Suitable coupler components are selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diamino-phenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}-amino)ethanol, 2-({3-[(2-hydroxyethylamino]-2-methoxy-5-methylphenyl}-amino) ethanol, 2-({3-[(2-hydroxyethyl)amino]-4,5-dimethylphenyl}amino)-ethanol, 2-[3-morpholin-4-ylphenyl)amino]ethanol, 3-amino-4-(2-methoxyethoxy)-5-methylphenylamine, 1-amino-3-bis(2-hydroxyethyl) aminobenzene, resorcinol, 2-methylresorcinol, 4-chlororesorcinol, 1,2,4-trihydroxy-benzene, 2-amino-3-hydroxypyridine, 3-amino-2-methylamino-6-methoxypyridine, 2,6-dihydroxy-3,4-dimethylpyridine, 3,5-diamino-2,6-dimethoxy-pyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or physiologically tolerated salts thereof. Particular preference is given here to resorcinol, 2-methylresorcinol, 5-amino-2-methyl-phenol, 3-aminophenol, 2-(2,4-diaminophenoxy)ethanol, 1,3-bis(2,4-diaminophenoxy)propane, 1-methoxy-2-amino-4-(2'-hydroxyethylamino)-benzene, 2-amino-3-hydroxypyridine and 1-naphthol and one of the physiologically tolerated salts thereof.

The coupler components are preferably used in an amount of 0.0001 to 10% by weight, preferably 0.001 to 5% by weight, in each case based on the entire composition.

Furthermore, the compositions according to the invention may comprise at least one further direct dye. These are dyes which are adsorbed directly onto the hair and do not require an oxidative process for the formation of the colour. Direct dyes are usually nitrophenylenediamines, nitroaminophenols, azo dyes, anthraquinones or indophenols.

The direct dyes are in each case preferably employed in an amount of 0.001 to 20% by weight, based on the entire preparation. The total amount of direct dyes is preferably at most 20% by weight. Direct dyes can be divided into anionic, cationic and nonionic direct dyes.

Preferred anionic direct dyes are the compounds known under the international names (INCI) or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

Preferred cationic direct dyes here are (a) cationic triphenylmethane dyes, such as, for example, Basic Blue 7, Basic Blue 26, Basic Violet 2 and Basic Violet 14, (b) aromatic systems which are substituted by a quaternary nitrogen group, such as, for example, Basic Yellow 57, Basic Red 76, Basic Blue 99, Basic Brown 16 and Basic Brown 17, and (c) direct dyes which contain a heterocycle which contains at least one quaternary nitrogen atom, as mentioned, for example, in Claims 6 to 11 of EP-A2-998 908, which is explicitly incorporated herein by way of reference.

Suitable nonionic direct dyes are, in particular, nonionic nitro and quinone dyes and neutral azo dyes.

The direct dyes employed can furthermore also be naturally occurring dyes, as are present, for example, in red henna, neutral henna, black henna, camomile blossom, sandalwood, black tea, alder buckthorn bark, sage, logwood, madder root, catechu, sedre and alkanet root.

A further possibility for changing the colour is offered by the use of colorants which comprise so-called oxo dye precursors. A first class of oxo dye precursors are compounds containing at least one reactive carbonyl group. This first class is known as component (Oxo1). A second class of oxo dye precursors is formed by CH-acidic compounds and compounds containing a primary or secondary amino group or hydroxyl group, which in turn are selected from compounds from the group formed by primary or secondary aromatic amines, nitrogen-containing heterocyclic compounds and aromatic hydroxyl compounds. This second class is known as component (Oxo2). The above-mentioned components (Oxo1) and (Oxo2) are generally not themselves dyes, and are therefore each taken individually alone not suitable for the dyeing of keratin-containing fibres. In combination, they form dyes in a non-oxidative process, so-called oxo dyeing. The resultant dyeings in some cases have colour fastnesses on the keratin-containing fibre which are comparable with those of oxidation dyeing.

The oxo dye precursors used are preferably a combination of at least one compound which contains at least one reactive carbonyl group (component (Oxo1))

with at least one compound (component Oxo2)

compounds selected from (Oxo2a) CH-acidic compounds and/or from (Oxo2b) compounds containing a primary or secondary amino group or hydroxyl group, selected from at least one compound from the group formed by primary or secondary aromatic amines, nitrogen-containing heterocyclic compounds and aromatic hydroxyl compounds.

Reactive carbonyl compounds as component (Oxo1) in the sense of the invention contain at least one carbonyl group as reactive group which reacts with component (Oxo2) with formation of a covalent bond. Preferred reactive carbonyl compounds are selected from compounds which carry at least one formyl group and/or at least one keto group, in particular at least one formyl group. Use can furthermore also be made in accordance with the invention as component (Oxo1) of compounds in which the reactive carbonyl group has been derivatised or masked in such a way that the reactivity of the carbon atom of the derivatised carbonyl group with component (Oxo2) is still present. These derivatives are preferably addition compounds a) of amines and derivatives thereof with formation of imines or oximes as addition compound b) of alcohols with formation of acetals or ketals as addition compound c) of water with formation of hydrates as addition compound (component (Oxo1) is in this case c) derived from an aldehyde) onto the carbon atom of the carbonyl group of the reactive carbonyl compound.

The reactive carbonyl component used for the purposes of oxo dyeing is very particularly preferably benzaldehyde and/or cinnamaldehyde and/or naphthaldehyde and/or at least one derivative of these above-mentioned aldehydes, which carry, in particular, one or more hydroxyl, alkoxy or amino substituents.

CH-acidic compounds are generally regarded as being compounds which carry a hydrogen atom bonded to an aliphatic carbon atom, where, owing to electron-withdrawing substituents, the corresponding carbon-hydrogen bond is activated. In principle, the choice of CH-acidic compounds is unlimited, so long as a compound which is visibly coloured to the human eye is obtained after condensation with the reactive carbonyl compounds of component (Oxo1). In accordance with the invention, these are preferably CH-acidic compounds which contain an aromatic and/or heterocyclic radical. The heterocyclic radical may in turn be alphatic or aromatic. The CH-acidic compounds are particularly preferably selected from heterocyclic compounds, in particular cationic, heterocyclic compounds.

The CH-acidic compounds of the oxo dye precursors of component (Oxo2a) are very particularly preferably selected from at least one compound from the group consisting of 2-(2-furoyl)acetonitrile, 2-(5-bromo-2-furoyl)-acetonitrile, 2-(5-methyl-2-trifluoromethyl-3-furoyl)acetonitrile, 3-(2,5-dimethyl-3-furyl)-3-oxopropanitrile, 2-(2-thenoyl)acetonitrile, 2-(3-thenoyl)-acetonitrile, 2-(5-fluoro-2-thenoyl)acetonitrile, 2-(5-chloro-2-thenoyl)acetonitrile, 2-(5-bro-2-thenoyl)acetonitrile, 2-(2,5-dimethylpyrrol-3-oyl)acetonitrile, 1H-benzimidazol-2-ylacetonitrile, 1H-benzothiazol-1-ylacetonitrile, 2-(pyrid-2-yl)acetonitrile, 2,6-bis(cyanomethyl)pyridine, 2-(indol-3-oyl)-acetonitrile, 8-canacetyl-7-methoxy-4-methylcoumarin, 2-(quinoxalin-2-yl)-acetonitrile, 1,2,3,3-tetramethyl-3H-indolium iodide, 1,2,3,3-tetramethyl-3H-indolium methanesulfonate, 2,3-dimethylbenzothiazolium iodide, 1,2-dihydrol, 3-diethyl-4,6-dimethyl-2-oxopyrimidinium hydrogensulfate, 1,2-dihydro-1,3,4,6-tetramethyl-2-thioxopyrimidinium chloride, 1,2-dihydro-1,3-diethyl-4-methyl-2-thioxopyrimidinium hydrogensulfate, 1,2-dihydro-1,3-dipropyl-4-methyl-2-thioxopyrimidinium chloride and 1,2-dihydro-1,3-dipropyl-4-methyl-2-thioxopyrimidinium hydrogensulfate.

Furthermore, component (Oxo2b) used can be at least one oxidation dye precursor containing at least one primary or secondary amino group and/or at least one hydroxyl group. Preferably suitable representatives are given under the explanation of the oxidation dye precursors. However, it is preferred in accordance with the invention for the compounds of component (Oxo2) to be selected only from CH-acidic compounds.

The above-mentioned compounds of component (Oxo1) and component (Oxo2) are, if they are used, in each case preferably used in an amount of 0.03 to 65 mmol, in particular 1 to 40 mmol, based on 100 g of the entire composition.

The compositions for the dyeing of hair which comprise at least one compound of the formula I, as described above, particularly preferably additionally comprise hydrogen peroxide. Particular preference is given to compositions of this type for the dyeing and optionally simultaneous lightening of keratin-containing fibres which comprise 0.5 to 15% by weight, preferably 1 to 12.5% by weight, particularly preferably 2.5 to 10% by weight and in particular 3 to 6% by weight of hydrogen peroxide (calculated as 100% $H_2O_2$).

The hydrogen peroxide can also be employed in the form of addition compounds thereof onto solid supports, preferably hydrogen peroxide itself is used. The hydrogen peroxide is employed as a solution or in the form of a solid addition compound of hydrogen peroxide onto inorganic or organic compounds, such as, for example, sodium perborate, sodium percarbonate, magnesium percarbonate, sodium percarbamide, polyvinylpyrrolidone $nH_2O_2$ (n is a positive integer greater than 0), urea peroxide and melamine peroxide.

Very particular preference is given to aqueous hydrogen peroxide solutions. The concentration of a hydrogen peroxide solution is determined on the one hand by the legal specifications and on the other hand by the desired effect; 6 to 12 percent solutions in water are preferably used.

For a colour change by means of lightening or bleaching of the substrate, for example the hair, at least one bleach enhancer is preferably additionally employed in cosmetic compositions besides the oxidants.

Bleach enhancers are preferably employed in order to increase the bleaching action of the oxidant, in particular the hydrogen peroxide. Suitable bleach enhancers are (BV-i) compounds which give rise to aliphatic peroxocarboxylic acids and/or optionally substituted perbenzoic acid under perhydrolysis conditions, and/or (BV-ii) carbonate salts and/or hydrogencarbonate salts, and/or (BV-iii) organic carbonates, and/or (BV-iv) carboxylic acids, and/or (BV-v) peroxo compounds.

Bleach enhancers are preferably peroxo compounds, in particular inorganic peroxo compounds. The bleach-enhancing peroxo compounds do not include any addition products of hydrogen peroxide onto other components nor hydrogen peroxide itself. In addition, the choice of peroxo compounds is not subject to any restrictions. Preferred peroxo compounds are peroxydisulfate salts, persulfate salts, peroxydiphosphate salts (in particular ammonium peroxydisulfate, potassium peroxydisulfate, sodium peroxydisulfate, ammonium persulfate, potassium persulfate, sodium persulfate, potassium peroxydiphosphate) and peroxides (such as barium peroxide and magnesium peroxide). Of these peroxo compounds, which can also be employed in combination, preference is given in accordance with the invention to the peroxydisulfates, in particular ammonium peroxydisulfate. Preference is given here to compositions for the dyeing and optionally simultaneous lightening of keratinic fibres which additionally comprise 0.01 to 2% by weight of at least one solid peroxo compound, which is selected from ammonium, alkali-metal and alkaline-earth metal persulfates, peroxomonosulfates and peroxydisulfates, where preferred compositions comprise peroxydisulfates, which are preferably selected from sodium peroxydisulfate and/or potassium peroxydisulfate and/or ammonium peroxydisulfate, and where preferred compositions comprise at least two different peroxydisulfates.

Particular preference is furthermore given to persulfates, in particular the mixture of potassium peroxosulfate, potassium hydrogensulfate and potassium sulfate known as Caro's salt.

The bleach enhancers are preferably present in the cosmetic compositions according to the invention in amounts of 5 to 30% by weight, in particular in amounts of 8 to 20% by weight, in each case based on the weight of the ready-to-use composition.

Furthermore, it has proven advantageous for the colorants and/or lightening compositions to comprise non-ionogenic surface-active substances.

Preference is given here to surface-active substances which have an HLB value of 5.0 or greater. For the definition of the HLB value, reference is expressly made to the comments in Hugo Janistyn, Handbuch der Kosmetika und Riechstoffe [Handbook of Cosmetics and Fragrances], Volume III: Die Körperpflegemittel [Body-Care Compositions], 2nd Edition, Dr. Alfred Hüthig Verlag Heidelberg, 1973, pages 68-78 and Hugo Janistyn, Taschenbuch der modernen Parfümerie und Kosmetik [Pocketbook of Modern Perfumery and Cosmetics], 4th Edition, Wissenschaftliche Verlagsgesellschaft m.b.H. Stuttgart, 1974, pages 466-474, and the original papers cited therein.

Owing to the simple processability, particularly preferred non-ionogenic surface-active substances here are substances which are commercially available in pure form as solids or liquids. The definition of purity in this connection does not relate to chemically pure compounds. Instead, in particular in the case of natural products, it is possible to employ mixtures of different homologues, for example having different alkyl chain lengths, as are obtained in the case of products based on natural fats and oils. Also in the case of alkoxylated products, mixtures of different degrees of alkoxylation are usually present. The term purity in this connection instead relates to the fact that the substances selected should preferably be free from solvents, extenders and other accompanying substances.

As further constituent, the compositions according to the invention may comprise, as hair colorant, at least one ammonium compound from the group ammonium chloride, ammonium carbonate, ammonium bicarbonate, ammonium sulfate and/or ammonium carbamate in an amount of 0.5 to 10, preferably 1 to 5% by weight, based on the entire composition.

Furthermore, the colorants and/or lightening compositions according to the invention may comprise further active compounds, assistants and additives, such as, for example, nonionic polymers, such as, for example, vinylpyrrolidone-vinyl acrylate copolymers, polyvinylpyrrolidone and vinylpyrrolidone-vinyl acetate copolymers and polysiloxanes, cationic polymers, such as quaternised cellulose ethers, polysiloxanes containing quaternary groups, dimethyldiallylammonium chloride polymers, acrylamide-dimethyldiallylammonium chloride copolymers, diethyl sulfate-quaternised dimethylaminoethyl methacrylate-vinylpyrrolidone copolymers, vinylpyrrolidone-imidazolinium methochloride copolymers and quaternised polyvinyl alcohol, zwitterionic and amphoteric polymers, such as, for example, acryl-amidopropyltrimethylammonium chloride-acrylate copolymers and octyl-acrylamide-methyl methacrylate-tert-butylaminoethyl methacrylate-2-hydroxypropyl methacrylate copolymers, anionic polymers, such as, for example, polyacrylic acids, crosslinked polyacrylic acids, vinyl acetate-crotonic acid copolymers, vinylpyrrolidone-vinyl acrylate copolymers, vinyl acetate-butyl maleate-isobornyl acrylate copolymers, methyl vinyl ether-maleic anhydride copolymers and acrylic acid-ethyl acrylate-N-tert-butylacrylamide terpolymers, thickeners, such as agar-agar, guar gum, alginates, xanthan gum, gum arabic, karaya gum, carob bean gum, linseed gums, dextrans, cellulose derivatives, for example methylcellulose, hydroxyalkylcellulose and carboxymethylcellulose, starch fractions and derivatives, such as amylose, amylopectin and dextrins, clays, such as, for example, bentonite, or fully synthetic hydrocolloids, such as, for example, polyvinyl alcohol, structurants, such as maleic acid and lactic acid, hair-conditioning compounds, such as phospholipids, for example soya lecithin, egg lecitin and cephalins, protein hydrolysates, in particular elastin, collagen, keratin, milk protein, soya protein and wheat protein hydrolysates, condensation products thereof with fatty acids and quaternised protein hydrolysates, perfume oils, dimethylisosorbide and cyclodextrins, solvents and solubilisers, such as ethanol, isopropanol, ethylene glycol, propylene glycol, propylene glycol, glycerin and diethylene glycol, fibre structure-improving active compounds, in particular mono-, di- and oligosaccharides, such as, for example, glucose, galactose, fructose, fruit sugar and lactose, quaternised amines, such as methyl-1-alkylamidoethyl-2-alkylimidazolinium methosulfate antifoams, such as silicones, dyes for tinting the composition, antidandruff active compounds, such as Piroctone Olamine, Zink Omadine and climbazole, light-protection agents, in particular derivatised benzophenones, cinnamic acid derivatives and triazines, substances for adjusting the pH, such as, for example, conventional acids, in particular edible acids and bases, active compounds, such as panthenol, pantothenic acid, allantoin, pyrrolidonecarboxylic acids and salts thereof, as well as bisabolol, vitamins, provitamins and vitamin precursors, in particular those from groups A, $B_3$, $B_5$, $B_6$, C, E, F and H, plant extracts, such as the extracts from green tea, oak bark, stinging nettles, witch hazel, hops, camomile, burdock root, horsetail, hawthorn, linden blossom, almonds, aloe vera, spruce needles, horse chestnut, sandalwood, juniper, coconut, mango, apricot, lime, wheat, kiwi, melon, orange, grapefruit, sage, rosemary, birch, mallow, cuckoo flower, wild thyme, yarrow, thyme, lemon balm, restharrow, coltsfoot, marshmallow, meristem, ginseng and ginger root, cholesterol, consistency modifiers, such as sugar esters, polyol esters or polyalkyl ethers, fats and waxes, such as spermaceti, beeswax, montan wax and paraffins, fatty alcohols and fatty acid esters, fatty acid alkanolamides, complexing agents, such as EDTA, NTA, β-alaninediacetic acid and phosphonic acids, swelling and penetration substances, such as glycerin, propylene glycol monoethyl ether, carbonates, hydrogencarbonates, guanidines, ureas and primary, secondary and tertiary phosphates, opacifiers, such as latex, styrene-PVP and styrene-acrylamide copolymers pearlescent agents, such as ethylene glycol mono- and distearate and PEG-3 distearate,
pigments,
stabilisers for hydrogen peroxide and other oxidants,
blowing agents, such as propane/butane mixtures, $N_2O$, dimethyl ether, $CO_2$ and air,
antioxidants.

The above-mentioned active compounds, assistants and additives may also be present in the preparations according to the invention, comprising at least one compound of the formula I and a vehicle which is suitable for cosmetic, pharmaceutical, dermatological preparations or household products, which are used, for example, for the dyeing of the skin or where the preparation as such is to be coloured. There are not restrictions regarding the ingredients of such preparations.

In preferred embodiments, the at least one compound of the formula I having the substituents defined or indicated as preferred or preferred individual compounds is typically employed in the preparations according to the invention for the dyeing of the skin or other substrates and for the dyeing of preparations per se in amounts of 0.05 to 10% by weight, preferably in amounts of 0.1% by weight to 5% by weight and particularly preferably in amounts of 0.5 to 2% by weight. The person skilled in the art is presented with absolutely no difficulties in selecting the amounts correspondingly depending on the intended action of the preparation.

The compounds of the formula I according to the invention can in addition be employed for the dyeing of household products, in particular household products packaged transparently. Household products include, for example, dishwashing compositions, cleaning compositions and detergents as well as air fresheners for rooms, cars and toilets.

The cosmetic, dermatological, pharmaceutical preparations or household products described which, in accordance with the invention, comprise at least one compound of the formula I may furthermore also comprise coloured pigments, where the layer structure of the pigments is not limited.

The coloured pigment should preferably be skin-coloured or brownish on use of 0.5 to 5% by weight. The choice of a corresponding pigment is familiar to the person skilled in the art.

Besides the compounds of the formula I and the optional other ingredients, the preparations may comprise further organic UV filters, so-called hydrophilic or lipophilic sun-protection filters, which are effective in the UVA region and/or UVB region and/or IR and/or VIS region (absorbers). These substances may be selected, in particular, from cinnamic acid derivatives, salicylic acid derivatives, camphor derivatives, triazine derivatives, β,β-diphenylacrylate derivatives, p-aminobenzoic acid derivatives and polymeric filters and silicone filters, which are described in the application WO-93/04665. Further examples of organic and also inorganic UV filters are indicated in the patent applications EP-A 0 487 404 and WO2009/077356. The said UV filters are usually named below in accordance with INCI nomenclature.

Particularly suitable for a combination are:

para-aminobenzoic acid and derivatives thereof: PABA, Ethyl PABA, Ethyl dihydroxypropyl PABA, Ethylhexyl dimethyl PABA, for example marketed by ISP under the name "Escalol 507", Glyceryl PABA, PEG-25 PABA, for example marketed by BASF under the name "Uvinul P25".

Salicylates: Homosalate marketed by Merck under the name "Eusolex HMS"; Ethylhexyl salicylate, for example marketed by Symrise under the name "Neo Heliopan OS", Dipropylene glycol salicylate, for example marketed by Scher under the name "Dipsal", TEA salicylate, for example marketed by Symrise under the name "Neo Heliopan TS".

β,β-Diphenylacrylate derivatives: Octocrylene, for example marketed by Merck under the name "Eusolex® OCR", by BASF under the name "Uvinul N539", Etocrylene, for example marketed by BASF under the name "Uvinul N35".

Benzophenone derivatives: Benzophenone-1, for example marketed under the name "Uvinul 400"; Benzophenone-2, for example marketed under the name "Uvinul D50"; Benzophenone-3 or Oxybenzone, for example marketed under the name "Uvinul M40"; Benzophenone-4, for example marketed under the name "Uvinul MS40"; Benzophenone-9, for example marketed by BASF under the name "Uvinul DS-49", Benzophenone-5, Benzophenone-6, for example marketed by Norquay under the name "Helisorb 11", Benzophenone-8, for example marketed by American Cyanamid under the name "Spectra-Sorb UV-24", Benzophenone-12 n-hexyl 2-(4-diethylamino-2-hydroxybenzoyl)benzoate or 2-hydroxy-4-methoxybenzophenone, marketed by Merck, Darmstadt, under the name Eusolex® 4360.

Benzylidenecamphor derivatives: 3-Benzylidenecamphor, for example marketed by Chimex under the name "Mexoryl SD", 4-Methylbenzylidenecamphor, for example marketed by Merck under the name "Eusolex 6300", benzylidenecamphorsulfonic acid, for example marketed by Chimex under the name "Mexoryl SL", Camphor benzalkonium methosulfate, for example marketed by Chimex under the name "Mexoryl SO", terephthalylidenedicamphorsulfonic acid, for example marketed by Chimex under the name "Mexoryl SX", Polyacrylamidomethylbenzylidenecamphor marketed by Chimex under the name "Mexoryl SW".

Phenylbenzimidazole derivatives: phenylbenzimidazolesulfonic acid, for example marketed by Merck under the name "Eusolex 232", disodium phenyl dibenzimidazole tetrasulfonate, for example marketed by Symrise under the name "Neo Heliopan AP".

Phenylbenzotriazole derivatives: Drometrizole trisiloxane, for example marketed by Rhodia Chimie under the name "Silatrizole", Methylenebis(benzotriazolyl)tetramethylbutylphenol in solid form, for example marketed by Fairmount Chemical under the name "MIXXIM BB/100", or in micronised form as an aqueous dispersion, for example marketed by Ciba Specialty Chemicals under the name "Tinosorb M".

Triazine derivatives: Ethylhexyltriazone, for example marketed by BASF under the name "Uvinul T150", Diethylhexylbutamidotriazone, for example marketed by Sigma 3V under the name "Uvasorb HEB", 2,4,6-tris(diisobutyl 4'-aminobenzalmalonate)-s-triazine or 2,4,6-Tris-(biphenyl)-1,3,5-triazine.

Anthraniline derivatives: Menthyl anthranilate, for example marketed by Symrise under the name "Neo Heliopan MA".

Imidazole derivatives: Ethylhexyldimethoxybenzylidenedioxoimidazoline propionate.

Benzalmalonate derivatives: polyorganosiloxanes containing functional benzalmalonate groups, such as, for example, Polysilicone-15, for example marketed by Hoffmann LaRoche under the name "Parsol SLX".

4,4-Diarylbutadiene derivatives: 1,1-Dicarboxy(2,2'-dimethylpropyl)-4,4-diphenylbutadiene.

Benzoxazole derivatives: 2,4-bis[5-(1-dimethylpropyl) benzoxazol-2-yl (4-phenyl)imino]-6-(2-ethylhexyl)imino-1, 3,5-triazine, for example marketed by Sigma 3V under the name Uvasorb K2A, and mixtures comprising this.

Piperazine derivatives, such as, for example, the compound

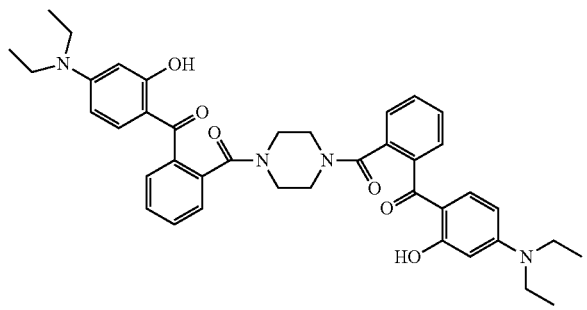 [SMILES: CCN(CC)c1ccc(C(=O)c2ccccc2C(=O)N2CCN(C(=O)c3ccccc3C(=O)c3ccc(N(CC)CC)cc3O)CC2)c(O)c1]

The compounds listed should only be regarded as examples. It is of course also possible to use other UV filters.

Suitable organic UV-protecting substances can preferably be selected from the following list: Ethylhexyl salicylate, Phenylbenzimidazolesulfonic acid, Benzophenone-3, Benzophenone-4, Benzophenone-5, n-Hexyl 2-(4-diethylamino-2-hydroxybenzoyl)benzoate, 4-Methylbenzylidenecamphor, Terephthalylidenedicamphorsulfonic acid, Disodium phenyldibenzimidazoletetrasulfonate, Methylenebis(benzotriazolyl)tetramethylbutylphenol, Ethylhexyl Triazone, Diethylhexyl Butamido Triazone, Drometrizole trisiloxane, Polysilicone-15, 1,1-Dicarboxy(2,2'-dimethylpropyl)-4,4-diphenylbutadiene, 2,4-Bis[5-1 (dimethylpropyl)benzoxazol-2-yl(4-phenyl)imino]-6-(2-ethylhexyl)-imino-1,3,5-triazine and mixtures thereof.

These organic UV filters are generally incorporated into formulations in an amount of 0.01 percent by weight to 20 percent by weight, preferably 1% by weight –10% by weight.

Combination with organic UV filters, as described above, or inorganic UV filters, as described above, is particularly advantageous if the compounds of the formula I, as described above, are employed for the protection of skin and hair against photoageing by light.

Besides the compounds of the formula I and the, where appropriate, other organic UV filters, as described above, the preparations may comprise further inorganic UV filters, so-called particulate UV filters.

These combinations with particulate UV filters are possible both as powder and also as dispersion or paste of the following types.

Preference is given here both to those from the group of the titanium dioxides, such as, for example, coated titanium dioxide (for example Eusolex® T-2000, Eusolex®T-AQUA, Eusolex®T-AVO, Eusolex®T-OLEO), zinc oxides (for example Sachtotec®), iron oxides or also cerium oxides and/or zirconium oxides.

Furthermore, combinations with pigmentary titanium dixoxide or zinc oxide are also possible, where the particle size of these pigments are greater than or equal to 200 nm, for example Hombitan® FG or Hombitan® FF-Pharma.

It may further be preferred for the preparations to comprise inorganic UV filters which have been after treated by conventional methods, as described, for example, in Cosmetics & Toiletries, February 1990, Vol. 105, pp. 53-64. One or more of the following aftertreatment components can be selected here: amino acids, beeswax, fatty acids, fatty acid alcohols, anionic surfactants, lecithin, phospholipids, sodium, potassium, zinc, iron or aluminium salts of fatty acids, polyethylenes, silicones, proteins (particularly collagen or elastin), alkanolamines, silicon dioxide, aluminium oxide, further metal oxides, phosphates, such as sodium hexametaphosphate, or glycerin.

Particulate UV filters preferably to be employed here are:
untreated titanium dioxides, such as, for example, the products Microtitanium Dioxide MT 500 B from Tayca; titanium dioxide P25 from Degussa,
Aftertreated micronised titanium dioxides with aluminium oxide and silicon dioxide aftertreatment, such as, for example, the product "Microtitanium Dioxide MT 100 SA from Tayca; or the product "Tioveil Fin" from Uniqema,
Aftertreated micronised titanium dioxides with aluminium oxide and/or aluminium stearate/laurate aftertreatment, such as, for example, Microtitanium Dioxide MT 100 T from Tayca, Eusolex T-2000 from Merck,
Aftertreated micronised titanium dioxides with iron oxide and/or iron stearate aftertreatment, such as, for example, the product "Microtitanium Dioxide MT 100 F" from Tayca,
Aftertreated micronised titanium dioxides with silicon dioxide, aluminium oxide and silicone aftertreatment, such as, for example, the product "Microtitanium Dioxide MT 100 SAS", from Tayca,
Aftertreated micronised titanium dioxides with sodium hexametaphosphates, such as, for example, the product "Microtitanium Dioxide MT 150 W" from Tayca.

The treated micronised titanium dioxides to be employed for the combination may also have been aftertreated with:
octyltrimethoxysilanes; such as, for example, the product Tego Sun T 805 from Degussa,
silicon dioxide; such as, for example, the product Parsol T-X from DSM,
aluminium oxide and stearic acid; such as, for example, the product UV-Titan M160 from Sachtleben,
aluminium and glycerin; such as, for example, the product UV-Titan from Sachtleben,
aluminium and silicone oils, such as, for example, the product UV-Titan M262 from Sachtleben,
sodium hexamethaphosphate and polyvinylpyrrolidone,
polydimethylsiloxanes, such as, for example, the product 70250 Cardre UF TiO2S13" from Cardre,
polydimethylhydrogensiloxanes, such as, for example, the product Microtitanium Dioxide USP Grade Hydrophobic" from Color Techniques.

The combination with the following products may furthermore also be advantageous:
Untreated zinc oxides, such as, for example, the product Z-Cote from BASF (Sunsmart), Nanox from Elementis
Aftertreated zinc oxides, such as, for example, the following products:
"Zinc Oxide CS-5" from Toshibi (ZnO aftertreated with polymethylhydro-genosiloxanes)
Nanogard Zinc Oxide FN from Nanophase Technologies
"SPD-Z1" from Shin-Etsu (ZnO aftertreated with a silicone-grafted acrylic polymer, dispersed in cyclodimethylsiloxanes
"Escalol Z100" from ISP (aluminium oxide-aftertreated ZnO dispersed in an ethylhexyl methoxycinnamate/PVP-hexadecene/methicone copolymer mixture)
"Fuji ZNO-SMS-10" from Fuji Pigment (ZnO aftertreated with silicon dioxide and polymethylsilesquioxane);
Untreated cerium oxide micropigment, for example with the name "Colloidal Cerium Oxide" from Rhone Poulenc
Untreated and/or aftertreated iron oxides with the name Nanogar from Arnaud.

For example, it is also possible to employ mixtures of various metal oxides, such as, for example, titanium dioxide and cerium oxide, with and without aftertreatment, such as, for example, the product Sunveil A from Ikeda. In addition, it is also possible to use mixtures of aluminium oxide, silicon dioxide and silicone-aftertreated titanium dioxide. zinc oxide mixtures, such as, for example, the product UV-Titan M261 from Sachtleben, in combination with the UV-protection agent according to the invention.

These inorganic UV filters are generally incorporated into the preparations in an amount of 0.1 percent by weight to 25 percent by weight, preferably 2% by weight –10% by weight.

By combination of one or more of the said compounds having a UV filter action, the protective action against harmful effects of the UV radiation can be optimised.

All said UV filters can also be employed in encapsulated form. In particular, it is advantageous to employ organic UV filters in encapsulated form. It may therefore be preferred for one or more of the above-mentioned UV filters to be in encapsulated form. It is advantageous here for the capsules to be so small that they cannot be observed with the naked eye. In order to achieve the above-mentioned effects, it is furthermore necessary for the capsules to be sufficiently stable and not to release the encapsulated active compound (UV filter) to the environment, or only to do so to a small extent.

Preferred preparations may also comprise at least one further cosmetic active compound, for example selected from antioxidants, anti-ageing active compounds, anti-cellulite active compounds, self-tanning substances, skin-lightening active compounds or vitamins.

Dyes according to the invention can furthermore be combined with all active compounds and assistants as listed systematically in WO2009/098139. In particular, these substances belong to the use categories mentioned therein "moisturisers and humectants", "desquamating agents", "agents for improving the barrier function", "depigmenting agents", "antioxidants", "dermo-relaxing or dermo-decontracting agents", "anti-glycation agents", "agents for stimulating the synthesis of dermal and/or epidermal macromolecules and/or for preventing their degradation", "agents for stimulating fibroblast or keratinocyte proliferation and/or keratinocyte differentiation", "agents for promoting the maturation of the horny envelope", "NO-synthase inhibitors", "peripheral benzodiazepine receptor (PBR) antagonists", "agents for increasing the activity of the sebaceous glands", "agents for stimulating the energy metabolism of cells", "tensioning agents", "fat-restructuring agents", "slimming agents", "agents for promoting the cutaneous microcirculation", "calmatives or anti-irritants", "sebo-regulating or anti-seborrhoic agents", "astringents", "cicatrising agents", "anti-inflammatory agents", "antiacne agents".

The protective action of preparations against oxidative stress or against the effect of free radicals can be improved if the preparations comprise one or more antioxidants, the person skilled in the art being presented with absolutely no difficulties in selecting antioxidants which act suitably quickly or with a time delay.

There are many proven substances known from the specialist literature which can be used as antioxidants, for example amino acids (for example glycine, histidine, tyrosine, tryptophan) and derivatives thereof, imidazoles, (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (for example buthionine sulfoximines, homo-cysteine sulfoximine, buthionine sulfones, penta-, hexa- and heptathionine sulfoximine) in very low tolerated doses (for example pmol to μmol/kg), and also (metal) chelating agents, (for example α-hydroxyfatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate) and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxybutyrophenone, quercitin, uric acid and derivatives thereof, mannose and derivatives thereof, zinc and derivatives thereof (for example ZnO, $ZnSO_4$), selenium and derivatives thereof (for example seleno-methionine), stilbenes and derivatives thereof (for example stilbene oxide, trans-stilbene oxide).

Suitable antioxidants are also compounds of the formulae A or B

A

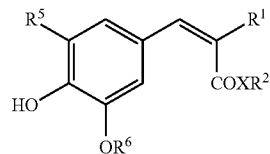

or

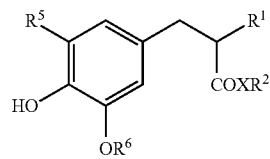

B in which $R^1$ can be selected from the group —$C(O)CH_3$, —$CO_2R^3$, —$C(O)NH_2$ and —$C(O)N(R^4)_2$, X denotes O or NH, $R^2$ denotes linear or branched alkyl having 1 to 30 C atoms, $R^3$ denotes linear or branched alkyl having 1 to 20 C atoms, $R^4$ in each case, independently of one another, denotes H or linear or branched alkyl having 1 to 8 C atoms, $R^5$ denotes H or linear or branched alkyl having 1 to 8 C atoms or linear or branched alkoxy having 1 to 8 C atoms and $R^6$ denotes linear or branched alkyl having 1 to 8 C atoms, preferably derivatives of 2-(4-hydroxy-3,5-dimethoxybenzylidene)malonic acid and/or 2-(4-hydroxy-3,5-dimethoxybenzyl)malonic acid, particularly preferably bis(2-ethylhexyl) 2-(4-hydroxy-3,5-dimethoxybenzylidene)malonate (for example Oxynex® ST Liquid) and/or bis(2-ethylhexyl) 2-(4-hydroxy-3,5-dimethoxy-benzyl)malonate (for example RonaCare® AP).

Furthermore, combination with bisisopropyl 2-(4-hydroxy-3-methoxy-benzylidene)malonate or bisisopropyl 2-(4-hydroxy-3-methoxybenzyl)malonate (hydrogenated diisopropyl vanilidene malonate) is preferred. An analogous situation applies to corresponding bisethyl esters. Mixtures of antioxidants are likewise suitable for use in the cosmetic preparations according to the invention. Known and commercial mixtures are, for example, mixtures comprising, as active ingredients, lecithin, L-(+)-ascorbyl palmitate and citric acid, natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Antioxidants of this type are usually employed in such compositions with the compounds according to the invention in percent by weight ratios in the range from 1000:1 to 1:1000, preferably in percent by weight ratios of 100:1 to 1:100.

Of the phenols which can be used in accordance with the invention, the polyphenols, some of which are naturally occurring, are of particular interest for applications in the pharmaceutical, cosmetic or nutrition sector. For example, the flavonoids or bioflavonoids, which are principally known as plant dyes, frequently have an antioxidant potential. Effects of the substitution pattern of mono- and dihydroxyflavones are described in K. Lemanska, H. Szymusiak, B. Tyrakowska, R. Zielinski, I. M. C. M. Rietjens; Current Topics in Biophysics 2000, 24 (2), 101-108, where it is observed that dihydroxyflavones containing an OH group adjacent to the keto function or OH groups in 3'4'- or 6,7- or 7,8-position have antioxidative properties, while other mono- and dihydroxyflavones in some cases do not have antioxidative properties.

Quercetin (cyanidanol, cyanidenolon 1522, meletin, sophoretin, ericin, 3,3',4',5,7-pentahydroxyflavone) is frequently mentioned as a particularly effective antioxidant (for example C. A. Rice-Evans, N. J. Miller, G. Paganga, Trends in Plant Science 1997, 2 (4), 152-159). K. Lemanska, H. Szymusiak, B. Tyrakowska, R. Zielinski, A. E. M. F. Soffers and I. M. C. M. Rietjens (Free Radical Biology & Medicine 2001, 31 (7), 869-881 investigate the pH dependence of the antioxidant action of hydroxyflavones. Of the structures investigated, quercetin exhibits the highest activity over the entire pH range.

Suitable anti-ageing active compounds, in particular for skin-care preparations, are preferably so-called compatible solutes. These are substances which are involved in the osmoregulation of plants or microorganisms and can be isolated from these organisms. The generic term compatible solutes here also encompasses the osmolytes described in German patent application DE-A-10133202. Suitable osmolytes are, for example, the polyols, methylamine compounds and amino acids and respective precursors thereof. Osmolytes in the sense of German patent application DE-A-10133202 are taken to mean, in particular, substances from the group of the polyols, such as, for example, myo-inositol, mannitol or sorbitol, and/or one or more of the osmolytically active substances mentioned below: taurine, choline, betaine, phosphorylcholine, glycerophosphorylcholines, glutamine, glycine, α-alanine, glutamate, aspartate, proline, and taurine. Precursors of these substances are, for example, glucose, glucose polymers, phosphatidylcholine, phosphatidylinositol, inorganic phosphates, proteins, peptides and polyamino acids. Precursors are, for example, compounds which are converted into osmolytes by metabolic steps.

Compatible solutes which are preferably employed in accordance with the invention are substances selected from the group consisting of pyrimidine-carboxylic acids (such as ectoin and hydroxyectoin), proline, betaine, glutamine, cyclic diphosphoglycerate, N.-acetylornithine, trimethylamine N-oxide di-myo-inositol phosphate (DIP), cyclic 2,3-diphosphoglycerate (cDPG), 1,1-diglycerin phosphate (DGP), β-mannosyl glycerate (firoin), β-mannosyl glyceramide (firoin-A) or/and dimannosyl diinositol phosphate (DMIP) or an optical isomer, derivative, for example an acid, a salt or ester, of these compounds, or combinations thereof.

Of the pyrimidinecarboxylic acids, particular mention should be made here of ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidine-carboxylic acid) and derivatives thereof.

Furthermore, the preparations according to the invention may comprise at least one self-tanner as further ingredient.

Advantageous self-tanners which can be employed are, inter alia: 1,3-dihydroxyacetone, glycerinaldehyde, hydroxymethylglyoxal, γ-dialdehyde, erythrulose, 6-aldo-D-fructose, ninhydrin, 5-hydroxy-1,4-naphtoquinone (juglone) or 2-hydroxy-1,4-naphtoquinone (lawsone). Very particular preference is given to 1,3-dihydroxyacetone, erythrulose or a combination thereof.

Preparations having self-tanner properties, in particular those which comprise dihydroxyacetone, tend towards malodours on application to the human skin, which are thought to be caused by degradation products of dihydroxyacetone itself or by products of side reactions and which are regarded as unpleasant by some users. It has been found that these malodours are prevented on use of formaldehyde scavengers and/or flavonoids. The preparation according to the invention comprising at least one self-tanner may therefore preferably also comprise formaldehyde scavengers and optionally flavonoids in order to improve the odour.

The formaldehyde scavenger is preferably selected from the group alkali-metal, alkaline-earth metal or ammonium disulfite. Particular preference is given to a preparation which comprises, in combination DHA Plus, a mixture of DHA, sodium disulfite and magnesium stearate.

DHA Plus is a product mixture which comprises sodium metabisulfite, synonymous with $Na_2S_2O_5$ or INCI: sodium disulfite, for the masking, elimination or neutralisation of the formaldehyde. The addition of sodium disulfite to finished formulations results in a significant reduction or suppression of the unpleasant odour. DHA Plus is marketed by Merck, Darmstadt.

The flavonoid optionally present in the preparation additionally acts as stabiliser for the self-tanner or the self-tanning substances and/or reduces or prevents or improves storage-dependent malodours, which may also arise through additives or assistants present.

The flavonoid preferably contains one or more phenolic hydroxyl groups which have been blocked by etherification or esterification. For example, hydroxyethyl-substituted flavonoids, such as, preferably, troxerutin, troxequercetin, troxeisoquercetin or troxeluteolin, and flavonoid sulfates or flavonoid phosphates, such as, preferably, rutin sulfates, have proven to be particularly suitable flavonoids here. In the sense of the use according to the invention, particular preference is given to rutin sulfate and troxerutin.

Very particular preference is given to the use of troxerutin. The preferred flavonoids have a non-positively charged flavan skeleton. It is thought that these flavonoids complex metal ions, such as, for example, $Fe^{2+}/Cu^{2+}$, and thus prevent or reduce autooxidation processes in fragrances or compounds whose degradation results in malodours.

Particular preference is given to a preparation which, besides the compounds of the formula I, comprise DHA Rapid and/or sodium metabisulfite. DHA Rapid is a product mixture comprising dihydroxyacetone and troxerutin, from Merck, Darmstadt.

Corresponding premixes and preparations which comprise formaldehyde scavengers and optionally flavonoids in order to improve the odour on the skin are described in the German patent application with the application file reference DE 10 2007 013 368.7, the contents of which in this respect expressly also belong to the disclosure content of the present application.

Combination of the compounds of the formula I according to the invention with self-tanning substances is particularly preferred in order to improve the colour effect which can be achieved by the self-tanner, for example by increasing the red proportion in the colour image in order to reduce the yellow impression. In addition, the compounds of the formula I according to the invention can reduce the malodour problem which is known for self-tanners and stabilise self-tanners.

The preparations may also comprise one or more further skin-lightening active compounds or synonymously depigmentation active compounds. Skin-lightening active compounds can in principle be all active compounds known to the person skilled in the art. Examples of compounds having skin-lightening activity are hydroquinone, kojic acid, arbutin, aloesin or rucinol. Preparations of this type enable, for example, the skin contrast between light and dark areas to be reduced. The skin thus appears to be more homogeneously coloured.

The preparations may also comprise anti-ageing active compounds and thus support the predominantly visual anti-ageing effect (protection against photoageing) by the compounds of the formula I according to the invention. This visual anti-ageing effect is based on an achievable homogeneous skin coloration. Suitable anti-ageing active compounds are, for example, the Merck-marketed products 5,7-dihydroxy-2-methylchromone, marketed under the trade name RonaCare® Luremine, or the products Ronacare® Isoquercetin, Ronacare® Tilirosid or Ronacare® Cyclopeptide 5.

The preparations to be employed may comprise vitamins as further ingredients. Preference is given to vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active compound), thiamine (vitamin $B_1$), nicotinic acid (niacin), pyridoxine, pyridoxal, pyridoxamine, (vitamin $B_6$), panthothenic acid, biotin, folic acid and cobalamine (vitamin $B_{12}$), particularly preferably vitamin A palmitate, vitamin C and derivatives thereof, DL-α-tocopherol, tocopherol E acetate, nicotinic acid, pantothenic acid and biotin. In the case of cosmetic application, vitamins are usually added with the flavonoid-containing premixes or preparations in ranges from 0.01 to 5.0% by weight, based on the total weight. Nutrition-physiological applications are oriented towards the respective recommended vitamin requirement.

The retinoids described are at the same time also effective anti-cellulite active compounds. A likewise known anti-cellulite active compound is caffeine.

The said constituents of the preparation can be incorporated in the usual manner, with the aid of techniques which are well known to the person skilled in the art.

Suitable preparations are those for external application, for example can be sprayed onto the skin as cream or milk (O/W, W/O, O/W/O, W/O/W), as lotion or emulsion, in the form of oily-alcoholic, oily-aqueous or aqueous-alcoholic gels or solutions. They can be in the form of solid sticks or formulated as an aerosol. Administration forms such as capsules, dragees, powders, tablet solutions or solutions are suitable for internal use.

Examples which may be mentioned of application form of the preparations to be employed are: solutions, suspensions, emulsions, PIT emulsions, pastes, ointments, gels, creams, lotions, powders, soaps, surfactant-containing cleansing preparations, oils, aerosols and sprays.

Preferred assistants originate from the group of preservatives, stabilisers, solubilisers, colorants, odour improvers.

Ointments, pastes, creams and gels may comprise the customary vehicles which are suitable for topical application, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary readily volatile, liquefied propellants, for example chlorofluorocarbons, propane/butane or dimethyl ether. Compressed air can also advantageously be used.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerin fatty acid esters, polyethylene glycols and fatty acid esters of sorbitan, or mixtures of these substances.

A preferred solubiliser in general is 2-isopropyl-5-methyl-cyclohexane-carbonyl-D-alanine methyl ester.

Suspensions may comprise the customary vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerin, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerin fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, powder make-up, emulsion make-up and wax make-up, and sunscreen, pre-sun and after-sun preparations.

The preferred preparation forms also include, in particular, emulsions.

Emulsions are advantageous and comprise, for example, the said fats, oils, waxes and other fatty substances, as well as water and an emulsifier, as usually used for a preparation of this type.

The lipid phase may advantageously be selected from the following group of substances:
  mineral oils, mineral waxes
  oils, such as triglycerides of capric or caprylic acid, furthermore natural oils, such as, for example, castor oil;
  fats, waxes and other natural and synthetic fatty substances, preferably esters of fatty acids with alcohols having a low carbon number, for example with isopropanol, propylene glycol or glycerin, or esters of fatty alcohols with alkanoic acids having a low carbon number or with fatty acids;
  silicone oils, such as dimethylpolysiloxanes, diethylpolysiloxanes, diphenylpolysiloxanes, and mixed forms thereof.

For the purposes of the present invention, the oil phase of the emulsions, oleogels or hydrodispersions or lipodispersions is advantageously selected from the group of esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, from the group of esters of aromatic carboxylic acid and saturated and/or unsaturated, branched and/or unbranched alcohols having a chain length of 3 to 30 C atoms. Ester oils of this type can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The mixture according to the invention may preferably comprise assistants, such as, for example, cosmetic oils (for example Caprylic/Capric Triglycerides, C12-15 Alkyl Benzoate, isopropyl myristate, Arylalkyl Benzoate, such as, for example, phenethyl benzoate (X-Tend 226), or oil components of the Cosmacol brand, such as Dimyristyl Tartrate, Tri C14-C15 Alkyl Citrate, C12-C13 Alkyl Lactate, Tridecyl Salicylate, C12-C13 Alkyl Octanoate, C12-C13 Alkyl Malate, C12-C13 Alkyl Citrate, C12-C13 Alkyl Tartrate), or polar-protic assistants (for example propylene glycol, glycerin, isopropanol, ethanol) or so-called solubilisers (for example butylphthalimides, isopropylphthalimides, dimethylisosorbides).

The oil phase may furthermore advantageously be selected from the group of branched and unbranched hydrocarbons and hydrocarbon waxes, silicone oils, dialkyl ethers, the group of saturated or unsaturated, branched or unbranched alcohols, and fatty acid triglycerides, specifically the triglycerin esters of saturated and/or unsaturated, branched and/or unbranched alkanecarboxylic acids having a chain length of 8 to 24, in particular 12-18 C atoms. The fatty acid triglycerides may, for example, advantageously be selected from the group of synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as sole lipid component of the oil phase.

The aqueous phase of the preparations to be employed optionally advantageously comprises alcohols, diols or polyols having a low carbon number, and ethers thereof, preferably ethanol, isopropanol, propylene glycol, glycerin, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerin, and, in particular, one or more thickeners, which may advantageously be selected from the group silicon dioxide, aluminium silicates, polysaccharides or derivatives thereof, for example hyaluronic acid, xanthan gum, hydroxypropylmethylcellulose, particularly advantageously from the group of the polyacrylates, preferably a polyacrylate from the group of the so-called Carbopols, for example Carbopol grades 980, 981, 1382, 2984, 5984, in each case individually or in combination.

In particular, mixtures of the above-mentioned solvents are used. In the case of alcoholic solvents, water may be a further constituent.

Emulsions are advantageous and comprise, for example, the said fats, oils, waxes and other fatty substances, as well as water and an emulsifier, as usually used for a formulation of this type.

In a preferred embodiment, the preparations to be employed comprise hydrophilic surfactants. The hydrophilic surfactants are preferably selected from the group of the alkylglucosides, acyl lactylates, betaines and coconut amphoacetates.

It is likewise advantageous to employ natural or synthetic raw materials and assistants or mixtures which are distinguished by an effective content of the active compounds used in accordance with the invention, for example Plantaren® 1200 (Henkel KGaA), Oramix® NS10 (Seppic).

The cosmetic and dermatological preparations may exist in various forms. Thus, they may be, for example, a solution, a water-free preparation, an emulsion or microemulsion of the water-in-oil (W/O) type or of the oil-in-water (O/W) type, a multiple emulsion, for example of the water-in-oil-in-water (W/O/W) type, a gel, a solid stick, an ointment or an aerosol. It is also advantageous to administer ectoins in encapsulated form, for example in collagen matrices and other conventional encapsulation materials, for example as cellulose encapsulations, in gelatine, wax matrices or liposomally encapsulated. In particular, wax matrices, as described in DE-A-43 08 282, have proven favourable. Preference is given to emulsions. O/W emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/W emulsions.

The co-emulsifiers selected are advantageously, for example, O/W emulsifiers, principally from the group of substances having HLB values of 11-16, very particularly advantageously having HLB values of 14.5-15.5, so long as the O/W emulsifiers have saturated radicals R and R'. If the O/W emulsifiers have unsaturated radicals R and/or R', or if isoalkyl derivatives are present, the preferred HLB value of such emulsifiers may also be lower or higher.

It is advantageous to select the fatty alcohol ethoxylates from the group of the ethoxylated stearyl alcohols, cetyl alcohols, cetylstearyl alcohols (cetearyl alcohols).

It is furthermore advantageous to select the fatty acid ethoxylates from the following group:

polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laurethyl-4 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerin fatty acid esters from the group polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/cprinate, polyethylene glycol (20) glyceryl oleate, polyethylene glycol (20) glyceryl isostearate, polyethylene glycol (18) glyceryl oleate (cocoate).

It is likewise favourable to select the sorbitan esters from the group polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

The following can be employed as optional W/O emulsifiers, but ones which may nevertheless be advantageous in accordance with the invention: fatty alcohols having 8 to 30 carbon atoms, monoglycerin esters of saturated and/or unsaturated, branched and/or unbranched alkanecarboxylic acids having a chain length of 8 to 24, in particular 12-18 C atoms, diglycerin esters of saturated and/or unsaturated, branched and/or unbranched alkanecarboxylic acids having a chain length of 8 to 24, in particular 12-18 C atoms, monoglycerin ethers of saturated and/or unsaturated, branched and/or unbranched alcohols having a chain length of 8 to 24, in particular 12-18 C atoms, diglycerin ethers of saturated and/or unsaturated, branched and/or unbranched alcohols having a chain length of 8 to 24, in particular 12-18 C atoms, propylene glycol esters of saturated and/or unsaturated, branched and/or unbranched alkanecarboxylic acids having a chain length of 8 to 24, in particular 12-18 C atoms, and sorbitan esters of saturated and/or unsaturated, branched and/or unbranched alkanecarboxylic acids having a chain length of 8 to 24, in particular 12-18 C atoms. Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate or PEG-30 dipolyhydroxystearate.

The preparation may comprise cosmetic adjuvants which are usually used in preparations of this type, such as, for example, thickeners, softeners, moisturisers, surface-active agents, emulsifiers, preservatives, antifoams, perfumes, waxes, lanolin, propellants, dyes and/or pigments, and other ingredients usually used in cosmetics.

The dispersant or solubiliser used can be an oil, wax or other fatty substance, a lower monoalcohol or a lower polyol or mixtures thereof. Particularly preferred monoalcohols or polyols include ethanol, i-propanol, propylene glycol, glycerin and sorbitol.

A preferred embodiment of the invention is an emulsion which is in the form of a protective cream or milk and comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerin, such as propylene glycol, and/or a polyol, such as glycerin, and oils, waxes and fatty acid esters, such as triglycerides of fatty acids.

The preparation may also be in the form of an alcoholic gel which comprises one or more lower alcohols or polyols, such as ethanol, propylene glycol or glycerin, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances. If a preparation is formulated as an aerosol, use is generally made of the customary propellants, such as alkanes, fluoroalkanes and chlorofluoroalkanes, preferably alkanes.

The compounds of the formula I, as described above are fluorescent emitters and can therefore likewise be employed in an electronic device.

The invention therefore furthermore relates to an electronic device comprising at least one compound of the formula I, as described above.

An electronic device here is taken to mean a device which comprises at least one layer which comprises at least one organic compound. However, the component here may also comprise inorganic materials or also layers built up entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers), organic plasmon emitting devices (D. M. Koller et al., Nature Photonics 2008, 1-4) and electrophotography devices, preferably organic electroluminescent devices (OLEDs) or organic light-emitting electrochemical cells (OLECs).

The organic electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers and/or charge-generation layers. It is likewise possible for interlayers, which have, for example, an exciton-blocking function, to be introduced between two emitting layers. However, it should be pointed out that each of these layers does not necessarily have to be present. A possible layer structure is, for example, the following: cathode/EML/interlayer/buffer layer/anode, where EML represents the emitting layer. The organic electroluminescent device here may comprise one emitting layer, or it may comprise a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 2005/011013). Furthermore, an optical coupling-out layer may have been applied to one or both of the electrodes.

Further organically functional materials which can be combined with the compounds of the formula I according to the invention for this specific application are, for example, host materials, matrix materials, electron-transport materials (ETM), electron-injection materials (EIM), hole-transport materials (HTM), hole-injection materials (HIM), electron-blocking materials (EBM), hole-blocking materials (HBM), exciton-blocking materials (ExBM) and/or emitters.

The invention therefore furthermore relates to a formulation or also composition comprising one or more compounds of the formula I, as described above and at least one further organically functional material selected from the group of the host materials, matrix materials, electron-transport materials, electron-injection materials, hole-transport materials, hole-injection materials, electron-blocking materials, hole-blocking materials, exciton-blocking materials and/or emitters.

In a preferred embodiment of the invention in the case of the use of the compounds of the formula I in an electronic device, the at least one compound of the formula I is employed in the emitting layer, preferably employed in a mixture with at least one further compound. It is preferred for the compound of the formula I in the mixture to be the emitting compound (the dopant). Preferred host materials are organic compounds whose emission is of shorter wavelength than that of the compound of the formula I or which do not emit at all.

The invention therefore furthermore relates to an organic electroluminescent device, as described above, characterised in that the at least one compound of the formula I, as described above, is employed as fluorescent emitter.

The proportion of the compound of the formula I in the mixture of the emitting layer is between 0.1 and 99.0% by weight, preferably between 0.5 and 50.0% by weight, particularly preferably between 1.0 and 20.0% by weight, in particular between 1.0 and 10.0% by weight. Correspondingly, the proportion of the host material in the layer is between 1.0 and 99.9% by weight, preferably between 50.0 and 99.5% by weight, particularly preferably between 80.0 and 99.0% by weight, in particular between 90.0 and 99.0% by weight.

Suitable host materials are various classes of substance. Preferred host materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 or WO 05/084082), the atropisomers (for example in accordance with the unpublished application EP 04026402.0) or the boronic acid derivatives (for example in accordance with the unpublished application EP 05009643.7). Particularly preferred host materials are selected from the classes of the oligoarylenes containing naphthalene, anthracene and/or pyrene or atropisomers of these compounds, the oligoarylenevinylenes, the ketones, the phosphine oxides and the sulfoxides. Very particularly preferred host materials are selected from the classes of the oligoarylenes containing anthracene and/or pyrene or atropisomers of these compounds, the phosphine oxides and the sulfoxides.

Particularly suitable matrix materials which can be employed in combination with the compounds of the formula I according to the invention are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-bis-carbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with the unpublished application DE 102008056688.8, diazaphosphole derivatives, for example in accordance with the unpublished application DE 102009022858.6, or indenocarbazole derivatives, for example in accordance with the unpublished applications DE 102009023155.2 and DE 102009031021.5.

Suitable phosphorescent compounds (triplet emitters) are, in particular, compounds which emit light or radiation, for example in the visible region and/or ultraviolet region and/or in the infrared region, on suitable excitation and in addition contain at least one atom having an atomic number greater than 20, preferably greater than 38 and less than 84, particularly preferably greater than 56 and less than 80. The phosphorescence emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as are used in accordance with the prior art for phosphorescent OLEDs and as are known to the person skilled in the art in the area of organic electro-luminescence are suitable, and the person skilled in the art will be able to use further phosphorescent complexes without inventive step.

Phosphorescent metal complexes preferably contain Ir, Ru, Pd, Pt, Os or Re. Preferred ligands for phosphorescent metal complexes are 2-phenyl-pyridine derivatives, 7,8-benzoquinoline derivatives, 2-(2-thienyl)pyridine derivatives, 2-(1-naphthyl)pyridine derivatives or 2-phenylquinoline derivatives. All these compounds may be substituted, for example by fluoro, cyano and/or trifluoromethyl substituents for blue. Auxiliary ligands are preferably acetylacetonate or picolinic acid.

Particularly suitable are complexes of Pt or Pd with tetradentate ligands, (US 2007/0087219), Pt-porphyrin complexes having an enlarged ring system (US 2009/0061681 A1) and Ir complexes, for example 2,3,7,8,12,13,17,18-octaethyl-21H, 23H-porphyrin-Pt(II), tetraphenyl-Pt(II) tetrabenzoporphyrin (US 2009/0061681), cis-bis(2-phenylpyridinato-N,$C^{2'}$)Pt(II), cis-bis(2-(2'-thienyl)pyridinato-N,$C^{3'}$)Pt(II), cis-bis(2-(2'-thienyl)-quinolinato-N,$C^{5'}$)Pt(II), (2-(4,6-difluorophenyl)pyridinato-N,$C^{2'}$)Pt(II) (acetylacetonate), or tris(2-phenylpyridinato-N,$C^{2'}$)Ir(III) (=Ir(ppy)$_3$, green), bis (2-phenylpyridinato-N,$C^{2'}$)Ir(III) (acetylacetonate) (=Ir (ppy)$_2$ acetylacetonate, green, US 2001/0053462 A1, Baldo, Thompson et. al. *Nature* 403, (2000), 750-753), bis(1-phenylisoquinolinato-N,$C^{2'}$)(2-phenylpyridinato-N,$C^{2'}$)-iridium (III), bis(2-phenylpyridinato-N,$C^{2'}$)(1-phenylisoquinolinato-N,$C^{2'}$)-iridium(III), bis(2-(2'-benzothienyl)pyridinato-N,$C^{3'}$) iridium(III) (acetylacetonate), bis(2-(4',6'-difluorophenyl) pyridinato-N,$C^{2'}$)iridium(III) (piccolinate) (Flrpic, blue), bis (2-(4',6'-difluorophenyl)pyridinato-N,$C^{2'}$)Ir(III) (tetrakis(1-pyrazolyl)borate), tris(2-(biphenyl-3-yl)-4-tert-butylpyridine)-iridium(III), (ppz)$_2$Ir(5phdpym) (US 2009/0061681 A1), (45ooppz)$_2$Ir(5phdpym) (US 2009/0061681 A1), derivatives of 2-phenyl-pyridine-Ir complexes, such as, for example, PQIr (=iridium(III) bis(2-phenylquinolyl-N, $C^{2'}$)acetylacetonate), tris(2-phenylisoquinolinato-N,C)Ir(III) (red), bis(2-(2'-benzo[4,5-a]thienyl)pyridinato-N,$C^{3'}$)Ir (acetylacetonate) ([Btp$_2$Ir(acac)], red, Adachi et al. *Appl. Phys. Lett.* 78 (2001), 1622-1624).

Likewise suitable are complexes of trivalent lanthanides, such as, for example, Tb$^{3+}$ and Eu$^{3+}$ (J. Kido et al. *Appl. Phys. Lett.* 65 (1994), 2124, Kido et al. Chem. Lett. 657, 1990, US 2007-0252517 A1) or phosphorescent complexes of Pt(II), Ir(I), Rh(I) with maleonitriledithiolate (Johnson et al., *JACS* 105, 1983, 1795), Re(I) tricarbonyl-diimine complexes (Wrighton, *JACS* 96, 1974, 998, inter alia), Os(II) complexes with cyano ligands and bipyridyl or phenanthroline ligands (Ma et al., *Synth. Metals* 94, 1998, 245).

Further phosphorescent emitters having tridentate ligands are described in U.S. Pat. No. 6,824,895 and U.S. Ser. No. 10/729,238. Red-emitting phosphorescent complexes are given in U.S. Pat. No. 6,835,469 and U.S. Pat. No. 6,830,828.

The compounds of the formula I, as described above, can preferably be employed in this application in combination with one or more further fluorescent materials (singlet emitters). Fluorescence in the sense of this invention is taken to mean the luminescence from an excited state having low spin multiplicity, i.e. from a spin state S=1.

Suitable fluorescent compounds (singlet emitters) are, in particular, compounds which emit light or radiation, for example in the visible region and/or ultraviolet region and/or in the infrared region, on suitable excitation.

Preferred dopants (emitters) are selected from the class of the monostyrylamines, the distyrylamines, the tristyrylamines, the tetrastyrylamines, the styrylphosphines, the styryl ethers and the arylamines.

A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

A further embodiment of the present invention in the specific application in electronic devices, relates to formulations comprising one or more of the compounds according to the invention and one or more solvents. The formulation is highly suitable for the production of layers from solution. Suitable and preferred solvents are, for example, toluene, anisole, xylenes, methyl benzoate, dimethylanisoles, trimethylbenzenes, tetralin, veratrols, tetrahydrofuran, chlorobenzene or dichlorobenzenes and mixtures thereof.

The organic electroluminescent device according to the invention can be used, for example, in displays or for lighting purposes, but also for medical or cosmetic applications.

The compounds according to the invention are suitable for use in light-emitting devices. These compounds can thus be employed in a very versatile manner. Some of the main areas of application here are display or lighting technologies. It is furthermore particularly advantageous to employ the compounds and devices comprising these compounds in the area of phototherapy.

Phototherapy or light therapy is used in many medical and/or cosmetic areas. The compounds according to the invention and the devices comprising these compounds can therefore be employed for the therapy and/or prophylaxis and/or diagnosis of all diseases and/or in cosmetic applications for which the person skilled in the art considers the use of phototherapy. Besides irradiation, the term phototherapy also includes photodynamic therapy (PDT) as well as disinfection and sterilisation in general. It is not only humans or animals that can be treated by means of phototherapy or light therapy, but also any other type of living or non-living matter. This includes, for example, fungi, bacteria, microbes, viruses, eukaryotes, prokaryotes, foods, drinks, water and drinking water.

The term phototherapy also includes any type of combination of light therapy and other types of therapy, such as, for example, treatment with active compounds. Many light therapies have the aim of irradiating or treating exterior parts of an object, such as the skin of humans and animals, wounds, mucous membranes, the eye, hair, nails, the nail bed, gums and the tongue. In addition, the treatment or irradiation according to the invention can also be carried out inside an object in order, for example, to treat internal organs (heart, lung, etc.) or blood vessels or the breast.

The therapeutic and/or cosmetic areas of application according to the invention are preferably selected from the group of skin diseases and skin-associated diseases or changes or conditions, such as, for example, psoriasis, skin ageing, skin wrinkling, skin rejuvenation, enlarged skin pores, cellulite, oily/greasy skin, folliculitis, actinic keratosis, precancerous actinic keratosis, skin lesions, sun-damaged and sun-stressed skin, crow's feet, skin ulcers, acne, acne rosacea, scars caused by acne, acne bacteria, photomodulation of greasy/oily sebaceous glands and their surrounding tissue, jaundice, jaundice of the newborn, vitiligo, skin cancer, skin tumours, Crigler-Naijar, dermatitis, atopic dermatitis, diabetic skin ulcers, and desensitisation of the skin.

Particular preference is given for the purposes of the invention to the treatment and/or prophylaxis of psoriasis, acne, cellulite, skin wrinkling, skin ageing, jaundice and vitiligo.

Further areas of application according to the invention for the compositions and/or devices comprising the compositions according to the invention are selected from the group of inflammatory diseases, rheumatoid arthritis, pain therapy, treatment of wounds, neurological diseases and conditions, oedema, Paget's disease, primary and metastasising tumours, connective-tissue diseases or changes, changes in the collagen, fibroblasts and cell level originating from fibroblasts in tissues of mammals, irradiation of the retina, neovascular and hypertrophic diseases, allergic reactions, irradiation of the respiratory tract, sweating, ocular neovascular diseases, viral infections particularly infections caused by herpes simplex or HPV (human papillomaviruses) for the treatment of warts and genital warts.

Particular preference is given for the purposes of the invention to the treatment and/or prophylaxis of rheumatoid arthritis, viral infections, and pain.

Further areas of application according to the invention for the compounds and/or devices comprising the compounds according to the invention are selected from winter depression, sleeping sickness, irradiation for improving the mood, the reduction in pain particularly muscular pain caused by, for example, tension or joint pain, elimination of the stiffness of joints and the whitening of the teeth (bleaching).

Further areas of application according to the invention for the compounds and/or devices comprising the compounds according to the invention are selected from the group of disinfections. The compounds according to the invention and/or the devices according to the invention can be used for the treatment of any type of objects (non-living matter) or subjects (living matter such as, for example, humans and animals) for the purposes of disinfection, sterilisation or preservation. This includes, for example, the disinfection of wounds, the reduction in bacteria, the disinfection of surgical instruments or other articles, the disinfection or preservation of foods, of liquids, in particular water, drinking water and other drinks, the disinfection of mucous membranes and gums and teeth. Disinfection here is taken to mean the reduction in the living microbiological causative agents of undesired effects, such as bacteria and germs.

For the purposes of the phototherapy mentioned above, devices comprising the compounds according to the invention preferably emit light having a wavelength between 250 and 1250 nm, particularly preferably between 300 and 1000 nm and especially preferably between 400 and 850 nm.

In a particularly preferred embodiment of the present invention, the compounds according to the invention are employed in an organic light-emitting diode (OLED) or an organic light-emitting electrochemical cell (OLEC) for the purposes of phototherapy. Both the OLED and the OLEC can have a planar or fibre-like structure having any desired cross section (for example round, oval, polygonal, square) with a single- or multilayered structure. These OLECs and/or OLEDs can be installed in other devices which comprise further mechanical, adhesive and/or electronic elements (for example battery and/or control unit for adjustment of the irradiation times, intensities and wavelengths). These devices comprising the OLECs and/or OLEDs according to the invention are preferably selected from the group comprising plasters, pads, tapes, bandages, cuffs, blankets, hoods, sleeping bags, textiles and stents.

The use of the said devices for the said therapeutic and/or cosmetic purpose is particularly advantageous compared with the prior art, since homogeneous irradiation of lower irradiation intensity is possible at virtually any site and at any time of day with the aid of the devices according to the invention using the OLEDs and/or OLECs. The irradiation can be carried out as an inpatient, as an outpatient and/or by the patient themselves, i.e. without initiation by medical or cosmetic specialists. Thus, for example, plasters can be worn under clothing, so that irradiation is also possible during working hours, in leisure time or during sleep. Complex inpatient/outpatient treatments can in many cases be avoided or their frequency reduced. The devices according to the invention may be intended for re-use or be disposable articles, which can be disposed of after use once, twice or three times.

Further advantages over the prior art are, for example, lower evolution of heat and emotional aspects. Thus, newborns being treated owing to jaundice typically have to be irradiated blindfolded in an incubator without physical contact with the parents, which represents an emotional stress situation for parents and newborns. With the aid of a blanket according to the invention comprising the OLEDs and/or OLECs according to the invention, the emotional stress can be reduced significantly. In addition, better temperature control of the child is possible due to reduced heat production of the devices according to the invention compared with conventional irradiation equipment.

Even without further comments, it is assumed that a person skilled in the art will be able to utilise the above description in the broadest scope. The preferred embodiments and examples should therefore merely be regarded as descriptive disclosure which is absolutely not limiting in any way. The complete disclosure content of all applications and publications mentioned above and below is incorporated into this application by way of reference. The percent by weight ratios of the individual ingredients in the preparations of the examples expressly belong to the disclosure content of the description and can therefore be utilised as features.

Further important features and advantages of the invention arise from the sub-claims and from the examples. It goes without saying that the features mentioned above and the features still to be explained below can be used not only in the respective combination indicated, but also in other combinations or in isolation without leaving the context of the present invention.

EXAMPLES

Example 1

Synthesis of 7-methyl-2,4-bis[1-(2,4,5-trimethoxyphenyl)meth-(Z)-ylidene]benzo[b]-1,4-dioxepin-3-one 0.7 g of potassium hydroxide (12.8 mmol, 2.2 eq.) are initially introduced in 8 ml of ethanol. 1 g of calone (5.6 mmol, 1 eq.) dissolved in 3 ml of ethanol are added. 2.4 g of 2,4,5-trimethoxybenzaldehyde (12.2 mmol, 2.2 eq.) are subsequently added. After 2 hours at 40° C., the mixture is cooled to 0° C., filtered and rinsed with 5 ml of ethanol. The solid obtained is recrystallised from 75 ml of boiling ethanol, giving 1.45 g of orange crystals as product.

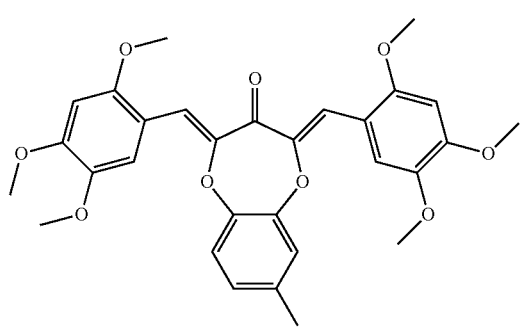

$^1$H-NMR (300 MHz, DMSO) δ=2.28 (s, Ar—CH$_3$), 3.80 (s, Ar—OCH$_3$), 3.81 (s, Ar—OCH$_3$), 3.88 (s, 2×Ar—OCH$_3$), 3.89 (s, 2×Ar—OCH$_3$), 6.78 (d, 2×CH—Ar, J=1.1 Hz), 7.05 (dd, Ar—H, J=1.5 Hz, J=8.2 Hz), 7.05 (d, Ar—H, J=1.5 Hz), 7.26 (m, 3×Ar—H) 8.04 (d, 2×Ar—H, J=3.2 Hz) ppm.

$^{13}$C-NMR (75 MHz, DMSO) δ=20.30, 55.78, 55.92, 55.97, 56.49, 97.44, 112.41, 112.99, 113.18, 113.29, 121.18, 121.74, 127.18, 136.69, 142.45, 145.89, 147.83, 149.81, 149.86, 151.80, 154.02, 182.22 ppm.

In ethanol, the substance exhibits intense absorption up to 539 nm

Example 2

Calone is reacted with 4-methoxybenzaldehyde analogously to the reaction conditions of Example 1, giving 2,4-bis[1-(4-methoxyphenyl)meth-(Z)-ylidene]-7-methylbenzo[b]-1,4-dioxepin-3-one

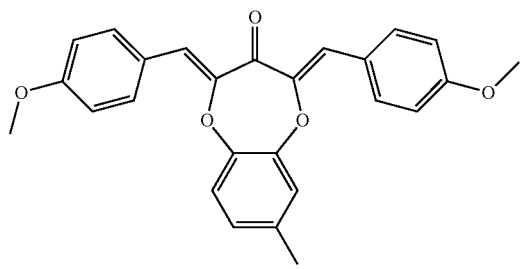

$^1$H-NMR (400 MHz, DMSO) δ=2.27 (s, Ar—CH$_3$), 3.82 (s, 2×Ar—OCH$_3$), 6.89 (d, 2×CH—Ar, J=8.2 Hz), 7.06 (m, Ar—H), 7.21 (d, Ar—H, J=1.5 Hz), 7.26 (d, Ar—H, J=8.2 Hz) 8.00 (d, 4×Ar—H, J=8.7 Hz) ppm.

$^{13}$C-NMR (75 MHz, DMSO) δ=20.11, 55.12, 111.87, 114.28, 119.11, 119.31, 121.25, 121.85, 126.93, 130.33, 132.56, 136.56, 145.56, 147.45, 149.83, 149.93, 160.17, 160.23, 182.44 ppm.

In ethanol, the substance exhibits intense absorption up to 478 nm

Example 3

Calone is reacted with 3,4-dimethoxybenzaldehyde analogously to the reaction conditions of Example 1, giving 2,4-bis[1-(3,4-dimethoxyphenyl)-meth-(Z)-ylidene]-7-methyl-benzo[b]-1,4-dioxepin-3-one.

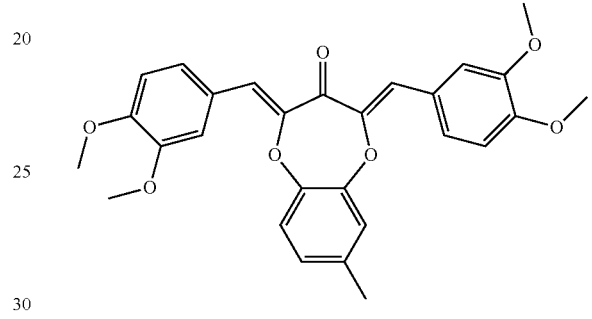

Example 4

Calone is reacted with 2,4-dimethoxybenzaldehyde analogously to the reaction conditions of Example 1, giving 2,4-bis[1-(2,4-dimethoxyphenyl)-meth-(Z)-ylidene]-7-methyl-benzo[b]-1,4-dioxepin-3-one.

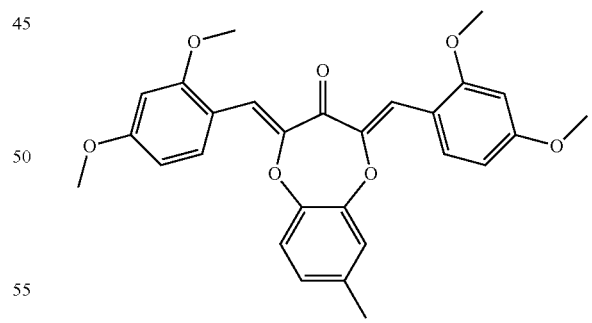

Example 5

Calone is reacted with 3,4,5-trimethoxybenzaldehyde analogously to the reaction conditions of Example 1, giving 7-methyl-2,4-bis[1-(3,4,5-tri-methoxyphenyl)meth-(Z)-ylidene]benzo[b]-1,4-dioxepin-3-one.

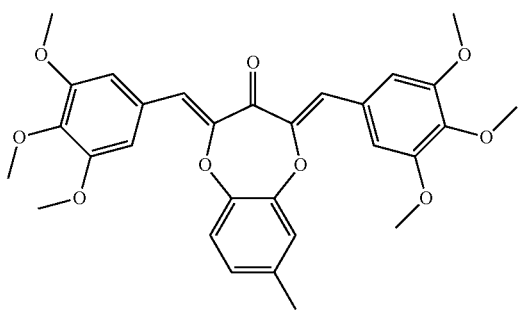

Example 6

Calone is reacted with 4-octyloxybenzaldehyde analogously to the reaction conditions of Example 1, giving 7-methyl-2,4-bis[1-(4-octyloxyphenyl)meth-(Z)-ylidene]benzo[b]-1,4-dioxepin-3-one.

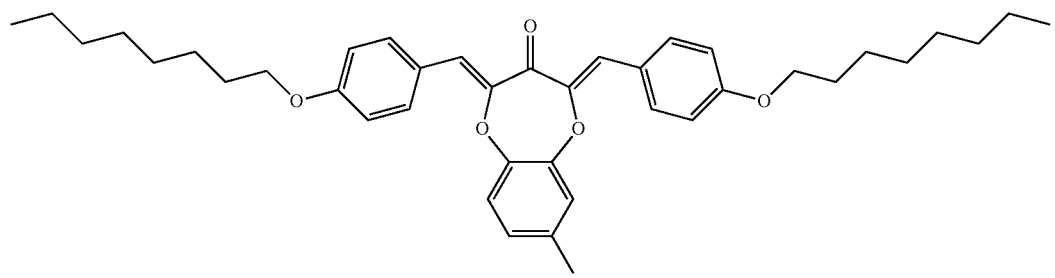 [SMILES: CCCCCCCCOc1ccc(/C=C2\Oc3ccc(C)cc3O/C(=C\c3ccc(OCCCCCCCC)cc3)C2=O)cc1]

Example 7

Calone is reacted with 4-phenoxybenzaldehyde analogously to the reaction conditions of Example 1, giving 7-methyl-2,4-bis[1-(4-phenoxyphenyl)meth-(Z)-ylidene]benzo[b]-1,4-dioxepin-3-one.

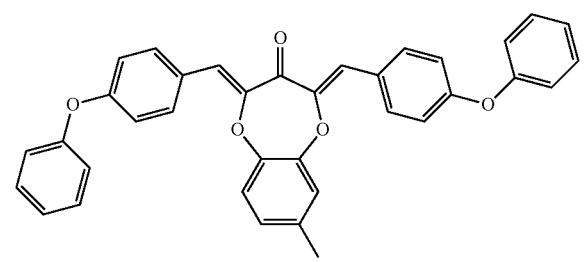 [SMILES: Cc1ccc2c(c1)O/C(=C\c1ccc(Oc3ccccc3)cc1)C(=O)/C(=C/c1ccc(Oc3ccccc3)cc1)O2]

Example 8

1.7 g of potassium hydroxide (30.9 mmol, 2.2 eq.) are initially introduced in 4 ml of ethanol. 2.5 g of calone (14.0 mmol, 1 eq.) dissolved in 2 ml of ethanol are added. 7.4 ml of 4-dibutylaminobenzaldehyde (30.9 mmol, 2.2 eq.) are subsequently added. After 16 hours at 50° C., a further 0.5 g of calone (0.16 mmol) are added, and the mixture is stirred at 50° C. for a further 24 hours. After addition of 100 ml of water and 200 ml of ethyl acetate, the mixture is extracted. The aqueous phase is extracted twice with 100 ml of ethyl acetate, the organic phases are combined, extracted with sat. sodium chloride solution and dried over sodium sulfate. The solvent is removed in vacuo, and the residue is purified by column chromatography, giving 1.45 g of product as red solid.

$^1$H-NMR (300 MHz, DMSO) δ=0.82 (t, 4×(CH$_2$)$_3$CH$_3$, J=7.3 Hz) 1.27 (m, 11×CH$_2$), 1.40 (m, 9×CH$_2$), 2.24 (s, Ar—CH$_3$) 3.49 (m, 4×CH$_2$), 6.86 (d, 2Ar—H J=8.3 Hz) 7.00 (dd, Ar—H, J=1.8 Hz, J=8.5 Hz), 7.19 (d, Ar—H, J=1.8 Hz), 7.24 (d, Ar—H, J=8.5 Hz), 7.35 (t, 4×Ar—H, J=8.4 Hz), 8.06 (d, 4×Ar—H, J=8.9 Hz) ppm.

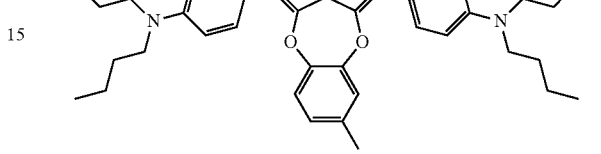

In ethanol, the substance exhibits intense absorption up to 609 nm

Example 9

Calone is reacted with 4-fluorobenzaldehyde analogously to the reaction conditions of Example 1, giving 2,4-bis[1-(4-fluorophenyl)meth-(Z)-ylidene]-7-methylbenzo[b]-1,4-dioxepin-3-one.

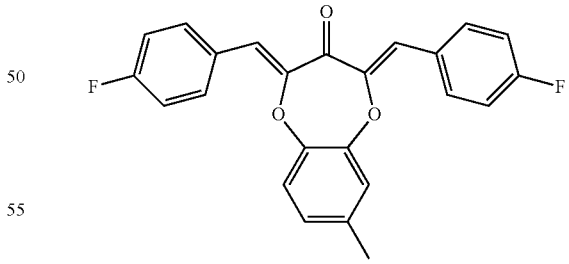

Example 10

Calone is reacted with 4-trifluoromethylbenzaldehyde analogously to the reaction conditions of Example 1, giving 7-methyl-2,4-bis[1-(4-trifluoro-methylphenyl)meth-(Z)-ylidene]benzo[b]-1,4-dioxepin-3-one.

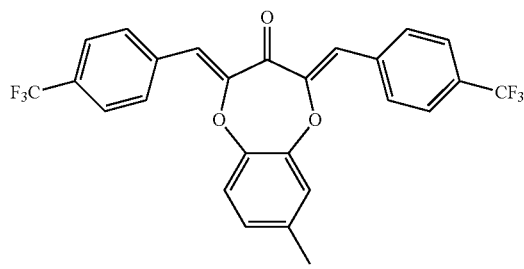 [SMILES: Cc1ccc2c(c1)O/C(=C\c1ccc(C(F)(F)F)cc1)C(=O)/C(=C/c1ccc(C(F)(F)F)cc1)O2]

Example 11 is reacted with 2,4,6-trimethoxybenzaldehyde analogously to the reaction conditions of Example 1, giving 7-methyl-2,4-bis[1-(2,4,6-trimethoxyphenyl)-meth-(Z)-ylidene]benzo[b]-1,4-dioxepin-3-one.

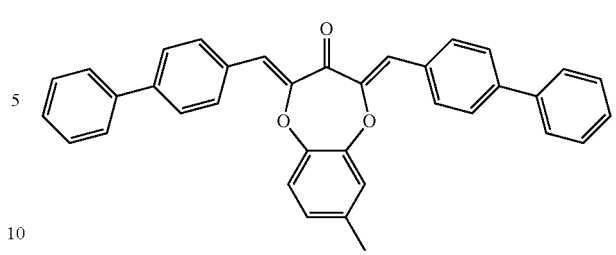

Example 14

Calone is reacted with naphthalene-1-carbaldehyde analogously to the reaction conditions of Example 1, giving 7-methyl-2,4-bis[1-naphthalen-1-yl-meth-(Z)-ylidene]benzo[b]-1,4-dioxepin-3-one.

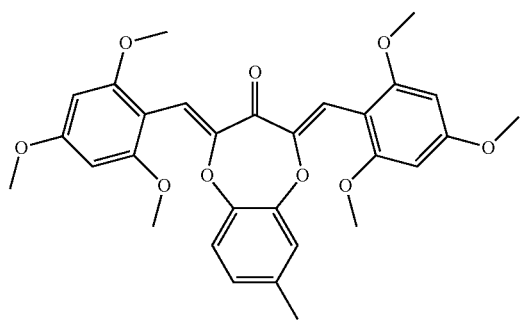

Example 12

Calone is reacted with 2,3,4-trimethoxybenzaldehyde analogously to the reaction conditions of Example 1, giving 7-methyl-2,4-bis[1-(2,3,4-tri-methoxyphenyl)meth-(Z)-ylidene]benzo[b]-1,4-dioxepin-3-one.

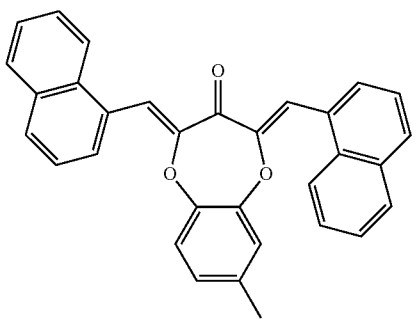

Example 15

Calone is reacted with 1-methylindole-3-carbaldehyde analogously to the reaction conditions of Example 1, giving 7-methyl-2,4-bis[1-(1-methyl-1H-indol-3-yl)meth-(Z)-ylidene]benzo[b]-1,4-dioxepin-3-one.

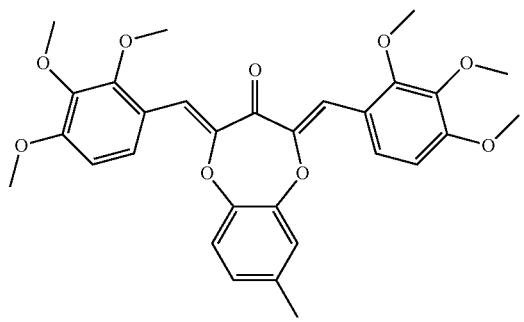

Example 13

Calone is reacted with biphenyl-4-carbaldehyde analogously to the reaction conditions of Example 1, giving 2,4-bis[1-biphenyl-4-ylmeth-(Z)-ylidene]-7-methylbenzo[b]-1,4-diosepin-3-one.

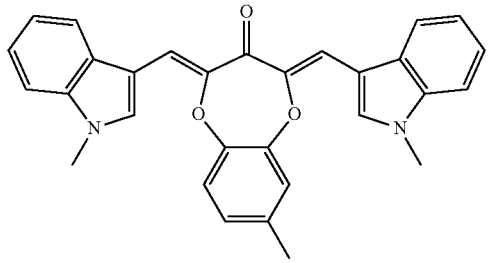 [SMILES: Cc1ccc2c(c1)O/C(=C\c1cn(C)c3ccccc13)C(=O)/C(=C/c1cn(C)c3ccccc13)O2]

Example 16

Calone is reacted with 9-ethylcarbazole-3-carbaldehyde analogously to the reaction conditions of Example 1, giving 7-methyl-4-[1-(9-ethyl-9H-carbazol-3-yl)meth-(Z)-ylidene]benzo[b]-1,4-dioxepin-3-one

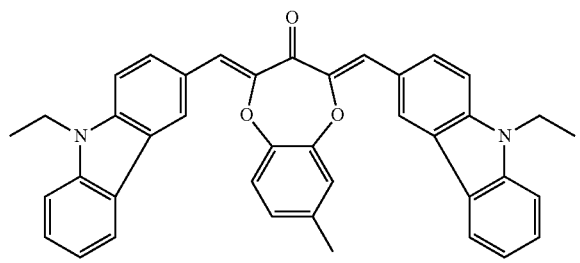 [SMILES: CCn1c2ccccc2c2cc(/C=C3\Oc4ccc(C)cc4O/C(=C\c4ccc5c(c4)c4ccccc4n5CC)C3=O)ccc21]

Example 17

Calone is reacted with 4-dimethylamino-2-methoxybenzaldehyde analogously to the reaction conditions of Example 1, giving 2,4-bis[1-(4-dimethyl-amino-2-methoxyphenyl)meth-(Z)-ylidene]-7-methylbenzo[b]-1,4-dioxepin-3-one.

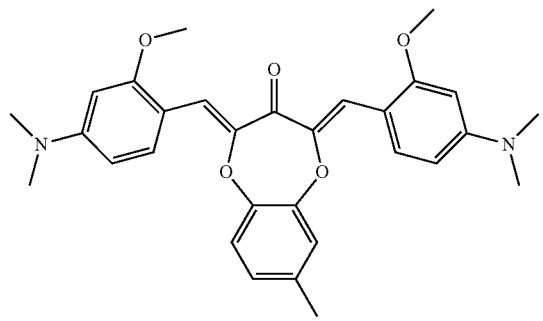

Example 18

Calone is reacted with 4-dimethylaminonaphthalene-1-carbaldehyde analogously to the reaction conditions of Example 1, giving 2,4-bis[1-(4-dimethylaminonaphthalen-1-yl)meth-(Z)-ylidene]-7-methylbenzo[b]-1,4-dioxepin-3-one.

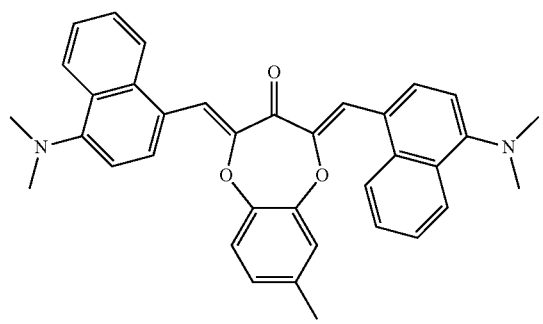

Example 19

Calone is reacted with 4-bromobenzaldehyde analogously to the reaction conditions of Example 1, giving 2,4-bis[1-(4-bromophenyl)meth-(Z)-ylidene]-7-methylbenzo[b]-1,4-dioxepin-3-one.

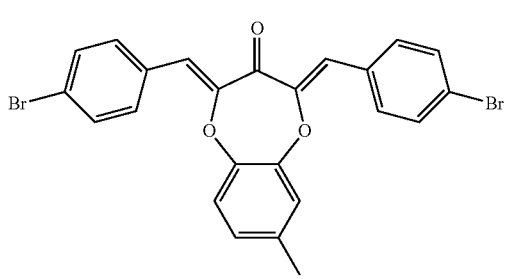 [SMILES: Cc1ccc2c(c1)O/C(=C\c1ccc(Br)cc1)C(=O)/C(=C/c1ccc(Br)cc1)O2]

Example 20

Calone is reacted with thiophene-2-carbaldehyde analogously to the reaction conditions of Example 1, giving 7-methyl-2,4-bis[1-thiophen-2-yl-meth-(Z)-ylidene]benzo[b]-1,4-dioxepin-3-one.

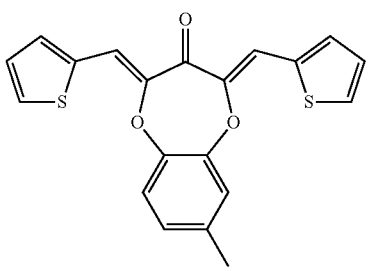 [SMILES: Cc1ccc2c(c1)O/C(=C\c1cccs1)C(=O)/C(=C/c1cccs1)O2]

Example 21

Calone is reacted with a mixture of 4-methoxybenzaldehyde and 4-(dibutyl-amino)benzaldehyde analogously to the reaction conditions of Example 1. The product mixture obtained is separated off by chromatography, giving, in particular, the compound 4-[1-(4-dibutylaminophenyl)meth-(Z)-ylidene]-2-[1-(4-methoxyphenyl)meth-(Z)-ylidene]-7-methylbenzo[b]-1,4-dioxepin-3-one.

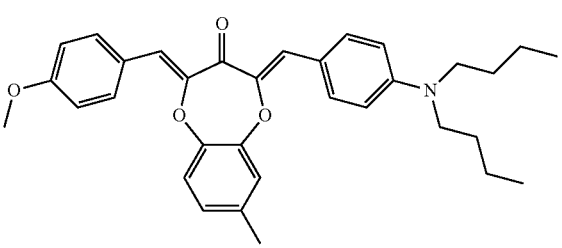 [SMILES: CCCCN(CCCC)c1ccc(/C=C2\Oc3cc(C)ccc3O/C(=C\c3ccc(OC)cc3)C2=O)cc1]

Example 22

Calone is reacted with 5-isopropyl-3,8-dimethylazulene-1-carbaldehyde analogously to the reaction conditions of Example 1, giving 2,4-bis[1-(5-isopropyl-3,8-dimethylazulen-1-yl)meth-(Z)-ylidene]-7-methylbenzo[b]-1,4-dioxepin-3-one.

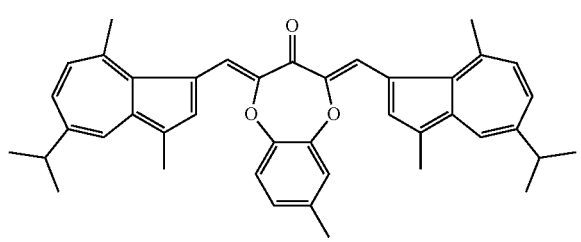 [SMILES: Cc1ccc2c(c1)O/C(=C\c1cc(C)c3cc(C(C)C)ccc(C)c1-3)C(=O)/C(=C/c1cc(C)c3cc(C(C)C)ccc(C)c1-3)O2]

Example 23

Calone is reacted with 4-carbazol-9-ylbenzaldehyde analogously to the reaction conditions of Example 1, giving 2,4-bis[1-(4-carbazolyl-9-yl-phenyl)meth-(Z)-ylidene]-7-methylbenzo[b]-1,4-dioxepin-3-one.

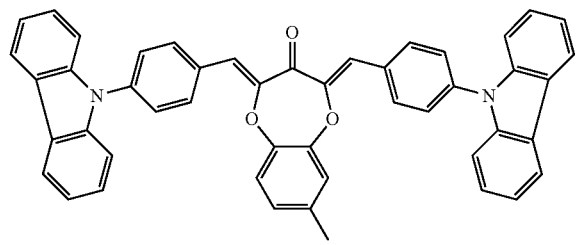 [SMILES: Cc1ccc2c(c1)O/C(=C\c1ccc(-n3c4ccccc4c4ccccc43)cc1)C(=O)/C(=C/c1ccc(-n3c4ccccc4c4ccccc43)cc1)O2]

Example 24

Calone is reacted with [1,1',3',1"]terphenyl-2'-carbaldehyde analogously to the reaction conditions of Example 1. The aldehyde can be synthesised correspondingly in accordance with the description by Bahaaldin Rashidzadeh et al, ARKIVOC 2008 (xvii) 167-172. 7-Methyl-2,4-bis[1-[1,1';3',1"]terphenyl-2'-ylmeth-(Z)-ylidene]benzo[b]-1,4-dioxepin-3-one is obtained. Ph=phenyl.

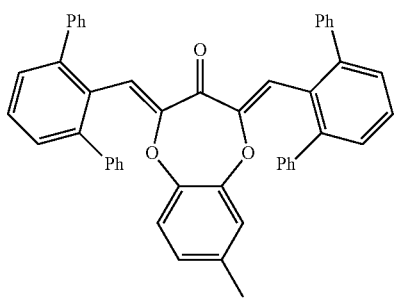 [SMILES: Cc1ccc2c(c1)O/C(=C\c1c(-c3ccccc3)cccc1-c1ccccc1)C(=O)/C(=C/c1c(-c3ccccc3)cccc1-c1ccccc1)O2]

Example 25

Calone is reacted with 3-(di-p-tolylamino)benzaldehyde analogously to the reaction conditions of Example 1, giving 2,4-bis[1-[4-(di-p-tolylamino)-phenyl]meth-(Z)-ylidene]-7-methylbenzo[b]-1,4-dioxepin-3-one.

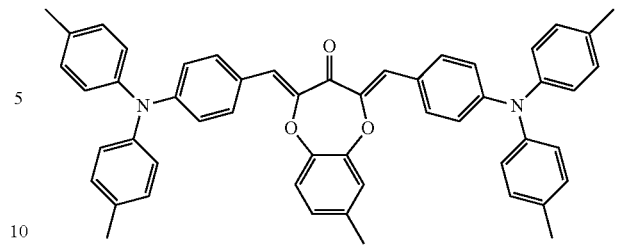

Example A

Absorption Strength

The measure used for the absorption strength is the so-called E1% value, and the half-value width of the absorption band in relation to the absorption maximum λmax indicated. The E1% value indicates the extinction at the absorption maximum extrapolated to a concentration of 1 g/100 ml. To this end, an absorption spectrum of the substance in ethanol is recorded in dilute solution. The values are compared with the reference spectra of curcumin and beta-carotene.

| Test substance | λmax [nm] | E1 % value | Half-value width [nm] |
|---|---|---|---|
| according to Example 1 | 437 | 505 | approx. 102 |
| according to Example 3 | 369 | 515 | approx. 100 |
| according to Example 8 | 484 | 571 | approx. 122 |
| Curcumin | 426 | 1507 | approx. 78 |
| Beta-carotene | 453 | 408 | approx. 88 |

Compared with curcumin and beta-carotene, the compounds of the formula I, for example the compounds of Examples 1, 3 and 8, cover a significantly greater spectral range. Although curcumin absorbs more intensely, it is, however, not thermally stable.

Example B

Thermal Stability

The thermal stability is determined with the aid of the thermographic method (instrument TGA Q5000 V3.10 Build 258, temperature range RT to 800° C., heating rate 10 K/min).

| Test substance | Temperature at which 98% of the weight was still present |
|---|---|
| according to Example 1 | 281° C. |
| according to Example 3 | 286° C. |
| according to Example 8 | 250° C. |
| Curcumin (comparison) | 223° C. |
| Beta-carotene (comparison) | 84° C. |

The thermal stabilities are excellent, meaning that high-temperature processing of the dyes of the formula I, for example the compounds of Examples 1, 3 and 8, such as, for example, incorporation into plastics, is also possible without decomposition.

Example C

Fluorescence Measurements

The substance concentrations in ethanol indicated in the table are measured using an Aminco Bowman 2 fluorescence spectrometer (cell thickness 1 cm; excitation 220-600 nm; emission 220-800 nm; spectral gap width (excitation) 4 nm, (emission) 8 nm; recording speed 10 nm/min; step width (excitation) 5 nm, (emission) 4 nm.

| Substance | Measurement concentration | Excitation | Emission |
|---|---|---|---|
| according to Example 1 | 0.00820 mg/ml | 350 nm, 290 nm, 245 nm | 412 nm |
| according to Example 3 | 0.00804 mg/ml | 230 nm | 322 nm |
| according to Example 8 | 0.00816 mg/ml | 260 nm | 320 nm |

Example D

Solubilities

The solubility determination was carried out in phenethyl benzoate (X-Tend 226):

| Test substance | Solubility in X-Tend 226: |
|---|---|
| according to Example 1 | 2.2% |
| according to Example 3 | 4.5% |
| according to Example 8 | 5.0% |

Formulation Examples

Example A-1

Hair Rinse

| | Per cent by weight [%] |
|---|---|
| Cetearyl Alcohol | 10 |
| Sunflowerseedamidopropyl Ethyldimonium Ethosulfate | 0.5 |
| Ceteareth-20 | 3.0 |
| Panthenol | 0.4 |
| Phenyl Trimethicone | 0.3 |
| Hydroxypropyl Guar Hydroxypropyltrimonium Chloride | 0.8 |
| Compound according to Example 1 | 1.0 |
| *Passiflora Incarnata* Seed Oil | 0.2 |
| Basic red 51 | 0.1 |
| Basic red 76 | 0.2 |
| Perfume | 1.0 |
| Preservative | q.s. |
| Citric Acid/Sodium Hydroxide | q.s. to pH 5.5 |
| Aqua | to 100 |

Example B-1

Shampoo

| | Per cent by weight [%] |
|---|---|
| Sodium Laureth Sulfate | 5.0 |
| Cocamidopropy Betaine | 5.0 |
| Lauroyl Glutamic Acid | 3.0 |
| Decyl Glucoside | 5.0 |
| Polyquaternium-10 | 0.5 |
| PEG-3 Distearate | 0.8 |
| Compound according to Example 8 | 0.5 |

| | Per cent by weight [%] |
|---|---|
| Evening primrose oil | 0.3 |
| Basic Red 51 | 0.1 |
| Ubiquinone | 0.1 |
| Benzyl Alcohol | 0.5 |
| Perfume | 1.0 |
| Preservative | q.s. |
| Sodium Chloride | 0.8 |
| Citric Acid/Sodium Hydroxide | q.s. to pH 5.5 |
| Aqua | to 100 |

Example C-1

Hair-Dyeing Recipes

| | 1 | 2 | 3 | 4 | 5 | 6 | 7 |
|---|---|---|---|---|---|---|---|
| Benzyl Alcohol | 2.5 | | | | | | |
| Propylene Carbonate | 10 | | | | | | |
| Ethanol | 5.0 | | | | | | |
| Hydroxyethylcellulose | 2.0 | | | | | | |
| Pirenoxine sodium CAS 51410-30-1 | 2.0 | | | | | | 2.0 |
| Tramsanguine CAS 34083-17-5 | | 1.0 | | | | 1.0 | |
| Cinnabarine CAS 606-59-7 | | | 1.0 | | | | |
| Cinnabaric acid CAS 146-90-7 | | | | 1.0 | | | |
| Resorcinol Blue CAS 71939-12-3 | | | | | 1.0 | | |
| Compound according to Example 1 | 1.0 | 1.0 | 2.0 | 1.0 | 1.0 | 0.5 | |
| Compound according to Example 8 | | | | | | 1.5 | 2.0 |
| Perfume | 1.0 | 1.0 | 1.0 | 1.0 | 1.0 | 1.0 | 1.0 |
| Preservative | q.s. | q.s. | q.s. | q.s. | q.s. | q.s. | q.s. |
| Citric Acid | q.s. to pH 5.5 | q.s. to pH 5.5 | q.s. to pH 5.5 | q.s. to pH 5.5 | q.s. to pH 5.5 | q.s. to pH 5.5 | q.s. to pH 5.5 |
| Aqua | to 100 | to 100 | to 100 | to 100 | to 100 | to 100 | to 100 |

Example D-1

Mild Transparent W/O Tanning Lotion

| Constituents/trade name | INCI | [% by weight] |
|---|---|---|
| A | | |
| Dow Corning 3225 C | CYCLOMETHICONE, DIMETHICONE COPOLYOL | 23.60 |
| Propyl 4-hydroxybenzoate | PROPYLPARABEN | 0.05 |
| Compound according to Example 3 | | 0.25 |
| B | | |
| Dihydroxyacetone | DIHYDROXYACETONE | 3.00 |
| Methyl 4-hydroxybenzoate | METHYLPARABEN | 0.15 |
| 1,2-Propanediol | PROPYLENE GLYCOL | 35.90 |
| Water, demineralised | AQUA (WATER) | 35.30 |
| Total | | 100.00 |

Example E-1

Coloured Shower Gel

| Ingredient | INCI | Concentration |
|---|---|---|
| Texapon NSO | Sodium Laureth Ether Sulfate | 10% |
| Dehyton K | Cocamidopropyl Betaine | 3% |
| Tagat L 2 | PEG-20 Glyceryl Laurate | 1% |
| Example 1 | | 0.001% |
| Example 8 | | 0.05%-0.1% |
| Water | Aqua | to 100 |

Example F-1

O-in-W emulsions for protection against visible radiation
In principle, other compounds of the formula I can also be used as an alternative to the use of the example substances shown in the table.

| | Figures in % by weight | | | | | | | | | |
|---|---|---|---|---|---|---|---|---|---|---|
| | 2-1 | 2-2 | 2-3 | 2-4 | 2-5 | 2-6 | 2-7 | 2-8 | 2-9 | 2-10 |
| Titanium dioxide | | 2 | 5 | | | | | | | 3 |
| Methylene Bis-Benztriazolyl Tetramethylbutylphenol | | | | | | 1 | 2 | 1 | | |
| Example 8 | 0.5 | 1 | 2 | 3 | 5 | | | | 1 | 1 |
| Example 1 | | | | | | 4 | 3 | 2 | 1 | 0.5 |
| Example 3 | 0.5 | 0.5 | 0.5 | | | | | | | |
| Example 4 | | | | | | | | 0.5 | 0.5 | 0.5 |
| 4-Methylbenzylidene Camphor | 2 | | 3 | | 4 | | 3 | | 2 | |
| Butyl Methoxydibenzoyl-methane | 1 | 3 | | 3 | 3 | | 3 | 3 | 3 | |
| Stearyl Alcohol (and) Steareth-7 (and) Steareth-10 | 3 | 3 | 3 | 3 | 3 | 3 | 3 | 3 | 3 | 3 |
| Glyceryl Stearate (and) Ceteth-20 | 3 | 3 | 3 | 3 | 3 | 3 | 3 | 3 | 3 | 3 |
| Glyceryl Stearate | 3 | 3 | 3 | 3 | 3 | 3 | 3 | 3 | 3 | 3 |
| Microwax | 1 | 1 | 1 | 1 | 1 | 1 | 1 | 1 | 1 | 1 |
| Cetearyl Octanoate | 11.5 | 11.5 | 11.5 | 11.5 | 11.5 | 11.5 | 11.5 | 11.5 | 11.5 | 11.5 |
| Caprylic/Capric Triglyceride | 6 | 6 | 6 | 6 | 6 | 6 | 6 | 6 | 6 | 6 |
| Oleyl Oleate | 6 | 6 | 6 | 6 | 6 | 6 | 6 | 6 | 6 | 6 |
| Propylene Glycol | 4 | 4 | 4 | 4 | 4 | 4 | 4 | 4 | 4 | 4 |
| Glyceryl Stearate SE | | | | | | | | | | |
| Stearic Acid | | | | | | | | | | |
| Persea Gratissima | | | | | | | | | | |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Tromethamine | | | 1.8 | | | | | | | |
| Water | to 100 | to 100 | to 100 | to 100 | to 100 | to 100 | to 100 | to 100 | to 100 | to 100 |

| | 2-11 | 2-12 | 2-13 | 2-14 | 2-15 | 2-16 | 2-17 | 2-18 |
|---|---|---|---|---|---|---|---|---|
| Titanium dioxide | 3 | | 2 | | | | 2 | 5 |
| Polysilicone 15 | | 1 | 0.5 | | | | | |
| Example 4 | 0.5 | 1.5 | 0.5 | 1 | | | | |
| Example 8 | | | | | 1 | 0.5 | 1.5 | 0.5 |
| Octocrylene | 5 | 5 | 5 | 5 | 5 | 5 | 5 | 5 |
| Example 1 | 0.5 | 1.5 | 1 | | 3 | | 2 | |
| Zinc oxide | | | | 2 | | | | |
| 4-Methylbenzylidene Camphor | | | | 3 | | | | |
| Butyl Methoxydibenzoylmethane | | | | 2 | | | | |
| Phenylbenzimidazole Sulfonic Acid | | | | | 1 | | | |
| Stearyl Alcohol (and) Steareth-7 (and) Steareth-10 | 3 | 3 | 3 | 3 | | | | |
| Glyceryl Stearate (and) Ceteth-20 | 3 | 3 | 3 | 3 | | | | |
| Glyceryl Stearate | 3 | 3 | 3 | 3 | | | | |
| Microwax | 1 | 1 | 1 | 1 | | | | |
| Cetearyl Octanoate | 11.5 | 11.5 | 11.5 | 11.5 | | | | |
| Caprylic/Capric Triglyceride | 6 | 6 | 6 | 6 | 14 | 14 | 14 | 14 |
| Oleyl Oleate | 6 | 6 | 6 | 6 | | | | |
| Propylene Glycol | 4 | 4 | 4 | 4 | | | | |
| Glyceryl Stearate SE | | | | | 6 | 6 | 6 | 6 |

| Figures in % by weight | | | | | | | | |
|---|---|---|---|---|---|---|---|---|
| Stearic Acid | | | | | 2 | 2 | 2 | 2 |
| Persea Gratissima | | | | | 8 | 8 | 8 | 8 |
| Propylparabene | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 |
| 1-methylhydantoine-2-imide | | | | | 3 | | | |
| Glycerin | | | | | 3 | 3 | 3 | 3 |
| Water | to 100 | to 100 | to 100 | to 100 | to 100 | to 100 | to 100 | to 100 |

The invention claimed is:

1. A compound of formula I

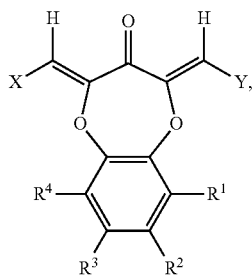

where $R^1$, $R^2$, $R^3$ and $R^4$ each, independently of one another, denotes H, $NO_2$, Hal, a straight-chain or branched alkyl group having 1 to 20 C atoms or a straight-chain or branched alkoxy group having 1 to 20 C atoms;

X and Y each, independently of one another, denote an aryl or heteroaryl group having 5 to 24 ring atoms which is unsub-stituted or mono- or polysubstituted by R, or a group of aryl and/or heteroaryl groups having 5 to 24 ring atoms which are unsubstituted or mono- or polysubstituted by R, where the aryl and/or heteroaryl groups in this group are each linked, independently of one another, singly or multiply, by a single bond, a double bond, conjugated double bonds, a C atom or by a unit of the formula $(CHR^5)_n$-$(Het)_o$-$(CHR^5)_p$;

R in each case, independently of one another on each occurrence, denotes D, Hal, alkyl, OH, O-alkyl, O-aryl, S-alkyl, $NH_2$, NHalkyl, $N(alkyl)_2$, $N(aryl)_2$, cycloalkyl, O-cycloalkyl, S-cycloalkyl, NH-cycloalkyl, $N(cycloalkyl)_2$, CN, $NO_2$, $Si(alkyl)_3$, $B(OR^6)_2$, $C(O)R^6$, $P(O)(R^6)_2$, $S(O)R^6$, $S(O)_2R^6$, a straight-chain or branched alkenyl group having 2 to 20 C atoms and one or more double bonds or a straight-chain or branched alkynyl group having 2 to 20 C atoms and at least one triple bond and optionally one or more double bonds;

$R^5$ in each case, independently of one another on each occurrence, denotes H, D, Hal, alkyl, OH, O-alkyl, O-aryl, S-alkyl, $NH_2$, NHalkyl, $N(alkyl)_2$, $N(aryl)_2$, cycloalkyl, O-cycloalkyl, S-cycloalkyl, NH-cycloalkyl, $N(cycloalkyl)_2$, CN, $NO_2$, $Si(alkyl)_3$, $B(OR^6)_2$, $C(O)R^6$, $C(O)_2R^6$, $P(O)(R^6)_2$, $S(O)R^6$, $S(O)_2R^6$, a straight-chain or branched alkenyl group having 2 to 20 C atoms and one or more double bonds or a straight-chain or branched alkynyl group having 2 to 20 C atoms and at least one triple bond and optionally one or more double bonds;

$R^6$ in each case, independently of one another, denotes H, D, OH, alkyl, aryl, cycloalkyl, Oalkyl, Oaryl or O-cycloalkyl;

alkyl denotes a straight-chain or branched alkyl group having 1 to 20 C atoms, which is optionally partially or fully substituted by halogen;

cycloalkyl denotes a cyclic saturated or partially unsaturated cycloalkyl group having 3 to 7 C atoms;

aryl denotes an aryl group having 6 to 10 C atoms, which is optionally mono- or polysubstituted by alkyl, Oalkyl, $N(alkyl)_2$ or Hal;

Hal denotes F, Cl, Br or I;

Het denotes O, S, —N=N—, NH or NR;

n denotes an integer from 0 to 5;

denotes 0 or 1;

p denotes an integer from 0 to 5; and n+o+p denotes at least the number 1, or a salt, tautomer, or steroisomer thereof, or a solvate thereof.

2. The compound of formula I according to claim 1, wherein three of the substituents $R^1$, $R^2$, $R^3$ or $R^4$ denote H and one of the substituents $R^1$, $R^2$, $R^3$ or $R^4$ denotes $NO_2$, Hal, a straight-chain or branched alkyl group having 1 to 20 C atoms or a straight-chain or branched alkoxy group having 1 to 20 C atoms.

3. The compound of formula I according to claim 1, wherein $R^1$, $R^3$ and $R^4$ denote H.

4. The compound of formula I according to claim 1, wherein X and Y each, independently of one another, denote an aryl or heteroaryl group having 5 to 18 ring atoms which is unsubstituted or mono- or polysubstituted by R.

5. The process for preparing a compound of formula I according to claim 1, comprising reacting a compound of formula II

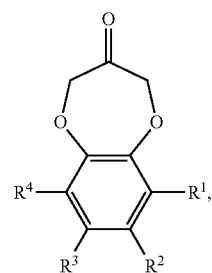

with a compound of formula IIIa and/or IIIb

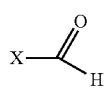

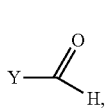

6. The conjugated, partially conjugated or non-conjugated polymer, oligomer or dendrimer containing one or more compounds of formula I according to claim 1, where the linking site between the at least one compound of formula I and the polymer, oligomer or dendrimer is at the position of the one or more radicals R of the compound of formula I.

7. The composition comprising one or more compounds of the formula I according to claim 1 and at least one additional compound.

8. The composition according to claim 7, comprising at least one vehicle which is suitable for cosmetic, pharmaceutical, or dermatological preparations or household products.

9. The composition according to claim 7, comprising at least one further organically functional material selected from the group consisting of host materials, matrix materials, electron-transport materials, electron-injection materials, hole-transport materials, hole-injection materials, electron-blocking materials, hole-blocking materials, exciton-blocking materials and emitters.

10. The process for preparing a composition according to claim 8, comprising mixing the at least one compound of the formula I with at least one vehicle which is suitable for cosmetic, pharmaceutical, or dermatological preparations or household products and optionally with one or more assistants and/or fillers.

11. The method for dyeing a product, comprising dyeing said product by a compound of formula I according to claim 1.

12. The method for protecting skin or hair against photo-ageing by light, comprising applying to the skin or hair a compound according to claim 1.

13. The electronic device, comprising at least one compound of formula I according to claim 1.

14. The electronic device according to claim 13, which is an organic electroluminescent device, an organically integrated circuit, an organic field-effect transistor, an organic thin-film transistor, an organic light-emitting transistor, an organic solar cell, an organic optical detector, an organic photoreceptor, an organic field-quench device, a light-emitting electrochemical cell or an organic laser diode.

15. The organic electroluminescent device, comprising at least one compound of formula I according to claim 1 as a fluorescent emitter.

16. The process according to claim 10, comprising dispersing or emulsifying or dissolving the at least one compound of the formula I with at least one vehicle which is suitable for cosmetic, pharmaceutical, or dermatological preparations or household products and optionally with one or more assistants and/or fillers.

17. The compound of formula I according to claim 1, wherein X and Y each, independently of one another, denote
   an aryl or heteroaryl group having 5 to 24 ring atoms which is unsubstituted or mono- or polysubstituted by R.

18. The compound of formula I according to claim 1, wherein X and Y each, independently of one another, denote
   a group of aryl and/or heteroaryl groups having 5 to 24 ring atoms which are unsubstituted or mono- or polysubstituted by R, where the aryl and/or heteroaryl groups in this group are each linked, independently of one another, singly or multiply, by a single bond, a double bond, conjugated double bonds, a C atom or by a unit of the formula $(CHR^5)_n$-$(Het)_o$-$(CHR^5)_p$.

19. The compound of formula I according to claim 1, wherein n+o+p denotes the number 1.

20. The compound of formula I according to claim 1, which is one of the following compounds

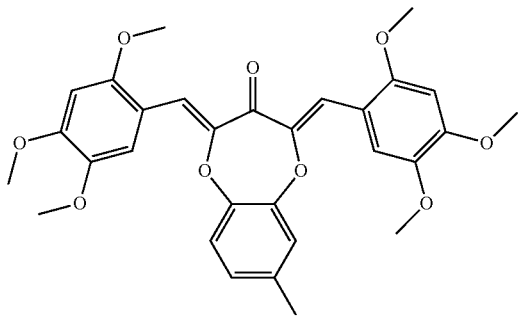

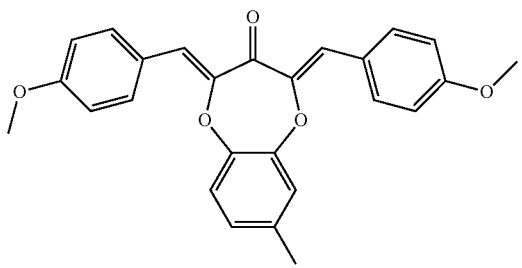

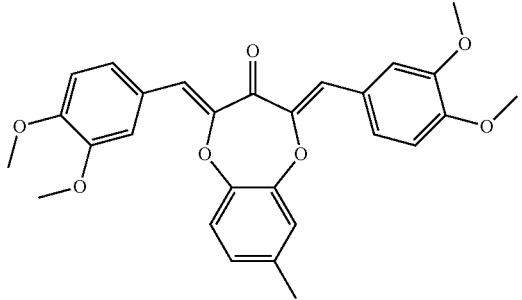

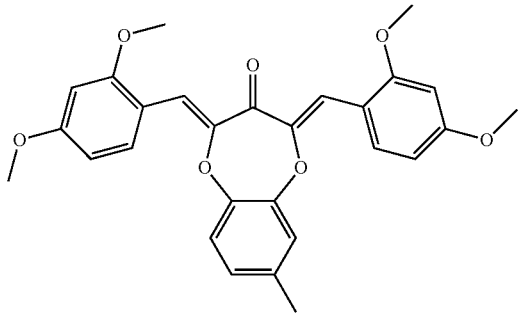

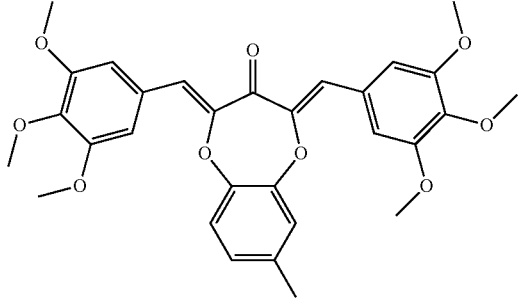

65
66
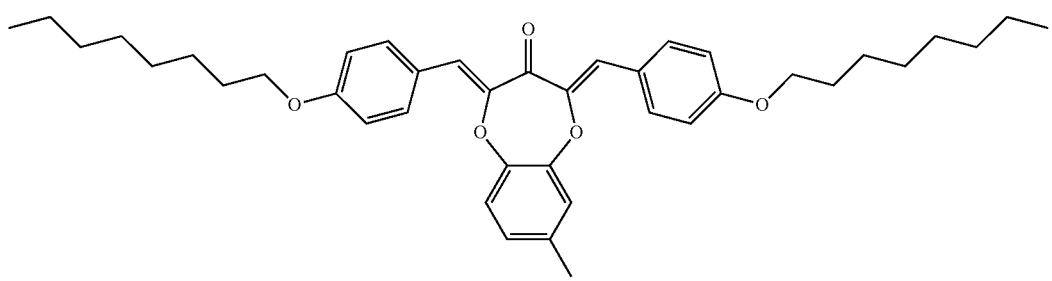 [SMILES: CCCCCCCCOc1ccc(/C=C2\Oc3ccc(C)cc3O/C(=C\c3ccc(OCCCCCCCC)cc3)C2=O)cc1]
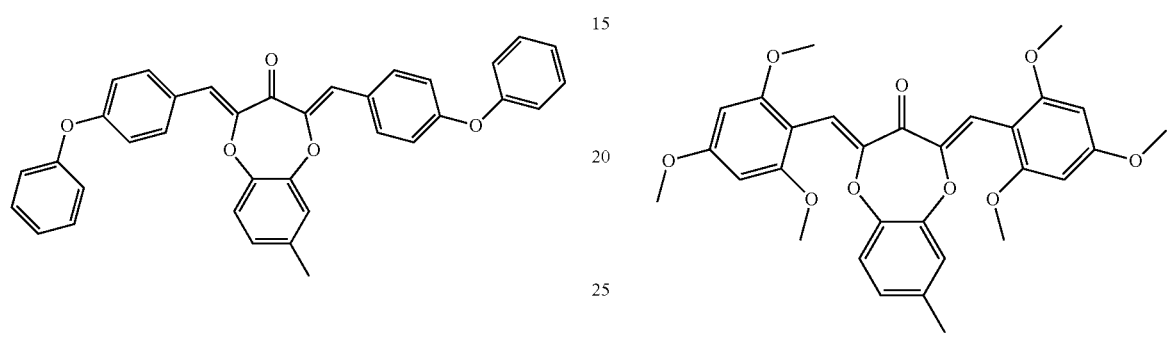
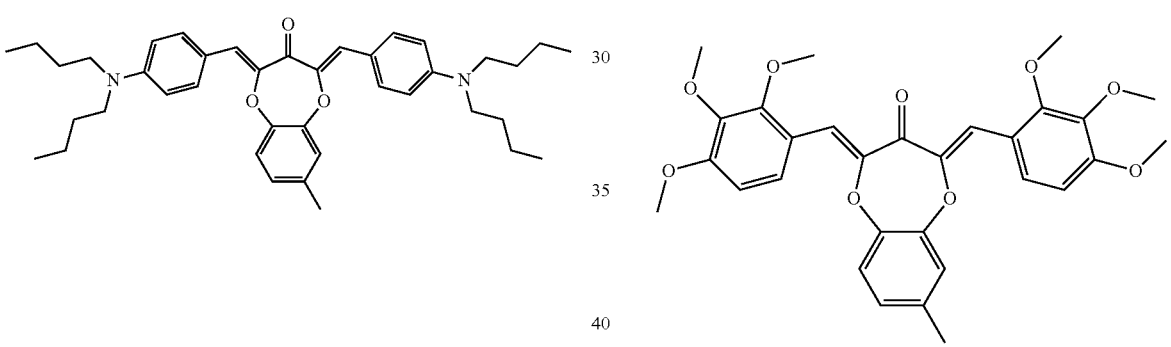
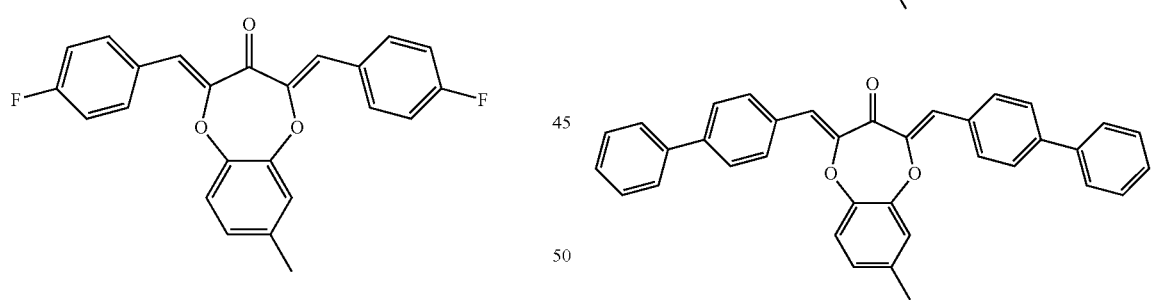
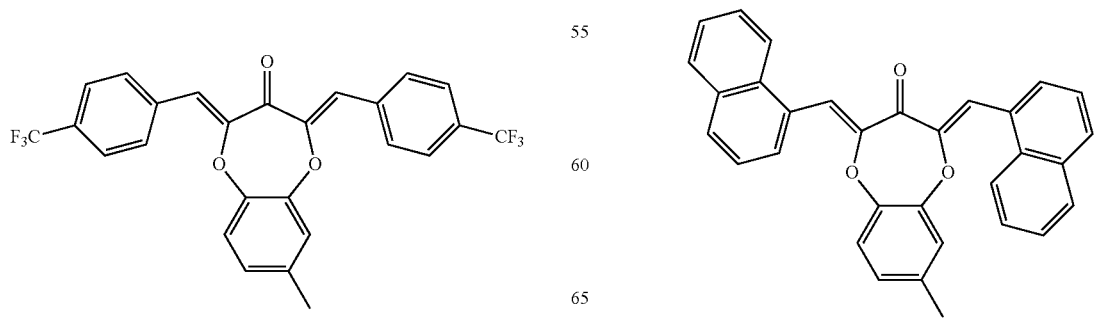

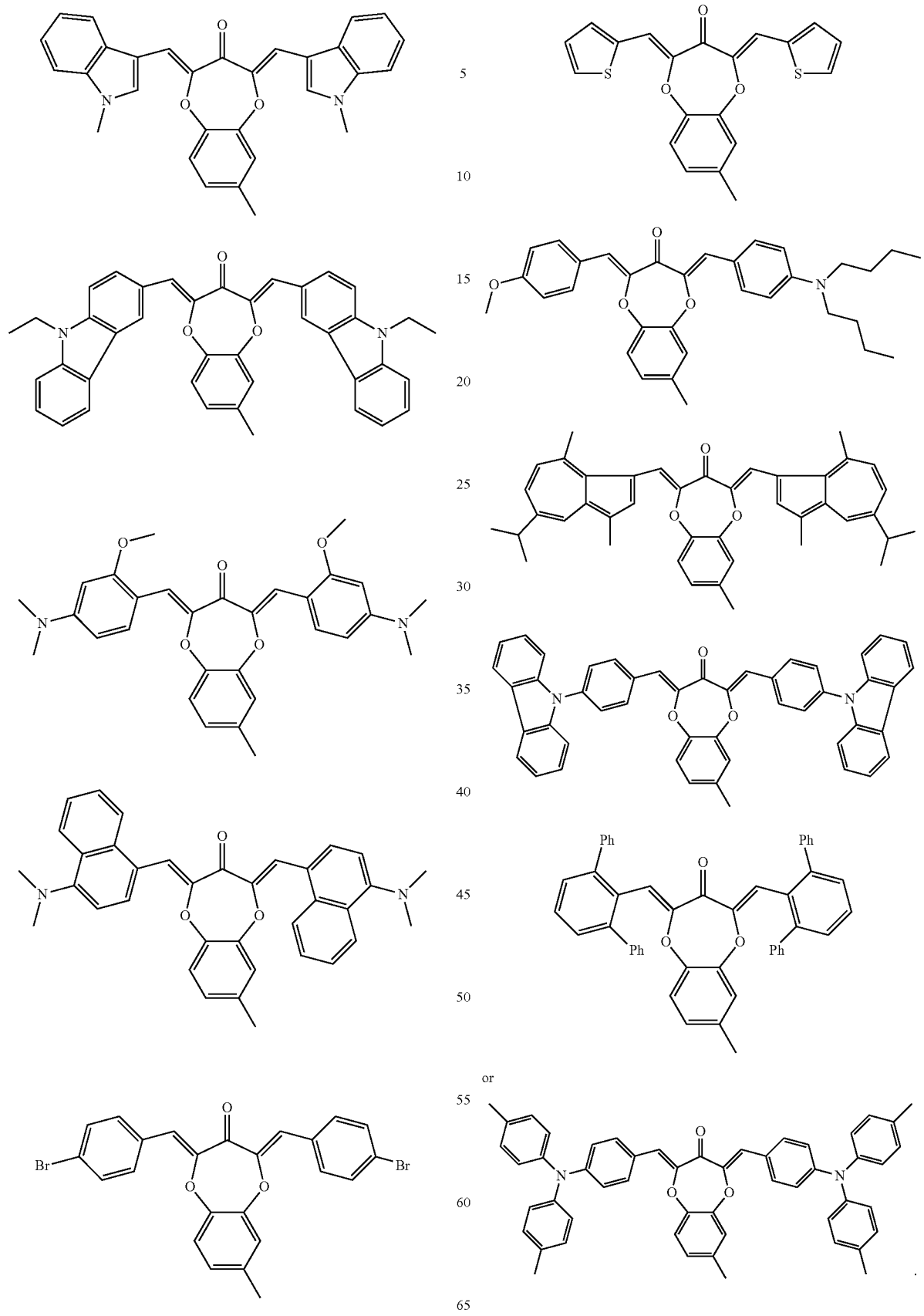

UNITED STATES PATENT AND TRADEMARK OFFICE
CERTIFICATE OF CORRECTION

PATENT NO. : 8,907,110 B2  
APPLICATION NO. : 14/351645  
DATED : December 9, 2014  
INVENTOR(S) : Thomas Rudolph et al.

Page 1 of 1

It is certified that error appears in the above-identified patent and that said Letters Patent is hereby corrected as shown below:

In the Claims

Column 62, Line 23 reads: "n denotes an integer from 0 to 5;" should read -- N denotes an integer from 0 to 5; --.

Column 62, Line 24 reads: "denotes 0 or 1;" should read -- O denotes 0 or 1; --.

Column 62, Line 25 reads: "p denotes an integer from 0 to 5; and" should read -- P denotes an integer from 0 to 5; and --.

Signed and Sealed this  
Seventh Day of July, 2015

Michelle K. Lee  
*Director of the United States Patent and Trademark Office*